(12) United States Patent
Eugen-Olsen

(10) Patent No.: US 6,902,884 B1
(45) Date of Patent: Jun. 7, 2005

(54) METHOD AND TOOL FOR PROGNOSTICATING HIV INFECTION IN A SUBJECT BY MEASURING SOLUBLE UROKINASE PLASMINOGEN ACTIVATOR RECEPTOR, DEGRADATION PRODUCTS THEREOF, AND UROKINASE PLASMINOGEN ACTIVATOR RECEPTOR

(75) Inventor: Jesper Eugen-Olsen, Hellerup (DK)

(73) Assignee: Virogates ApS, Kbh K (DK)

( * ) Notice: Subject to any disclaimer, the term of this patent is extended or adjusted under 35 U.S.C. 154(b) by 39 days.

(21) Appl. No.: 10/148,492

(22) PCT Filed: Nov. 27, 2000

(86) PCT No.: PCT/DK00/00651

§ 371 (c)(1),
(2), (4) Date: Aug. 22, 2002

(87) PCT Pub. No.: WO01/38871

PCT Pub. Date: May 31, 2001

(30) Foreign Application Priority Data

Nov. 25, 1999 (DK) .......................................... 1999 01687

(51) Int. Cl.[7] ................................................ C12Q 1/70
(52) U.S. Cl. ........................... 435/5; 435/7.1; 435/7.92; 435/7.94; 435/7.95; 435/215; 435/974; 435/975; 436/531
(58) Field of Search .......................... 435/5, 7.1, 7.92, 435/7.94, 7.95, 215, 974, 975; 436/531

(56) References Cited

U.S. PATENT DOCUMENTS 4,845,026 A * 7/1989 Kung et al. ...................... 435/5
5,459,078 A * 10/1995 Kline et al. .................. 436/518

FOREIGN PATENT DOCUMENTS

WO WO-01/38871 A1 5/2001
WO WO-02/095411 A1 11/2002

OTHER PUBLICATIONS

Stephens et al. Clinical Chemistry vol. 43, No. 10 (1997), pp. 1868–1876.*
Hengge et al. AIDS Vo. 12 (1998), pp. F225–F234.*
Dekkers, Pascale E.P., et al., "Upregulation of Monocyte Urokinase plasminogen Activator Receptor during Human Endotoxemia", Infection and Immunity, vol. 68, No. 4, Apr. 2000, pp. 2156–2160.
Coleman, James L., et al., "*Borrelia burgdorferi* and Other Bacterial Products Induce Expression and Release of the Urokinase Receptor (CD87)1", The Journal of Immunology, vol. 166, 2001, pp. 473–480.
Florquin, et al., "Release of urokinase plasminogen activator receptor during urosepsis and endotoxemia", Kidney International, vol. 59, 2001, pp. 2054–2061.

Fauser, Susanne, et al., "Lesion associated expression of urokinase-type plasminogen activator receptor (uPAR, CD87) in human cerebral malaria", Journal of Neuroimmunology, vol. 111, 2000, pp. 234–240.
Heegaard, C.W., et al., "Plasminogen Activators in Bovine Milk During Mastitis, an Inflammatory Disease", Fibrinolysis, vol. 8, 194, pp. 22–30.
Todd, Robert, F., et al., "Bacterial lipopolysaccharide, phorbol myristate acetate, and muramyl dipeptide stimulate the expression of a human monocyte surface antigen", The Journal of Immunology, vol. 135, No. 6, Dec. 1985, pp. 3869–3877.
Eugen–Olsen, J., et al., "The serum level of soluble urokinase receptor is elevated in tuberculosis patients and predicts mortality during treatment: a community study from Guinea–Bissau" Int. J. Tuberc. Lung Dis., vol. 6, No. 8, 2002, pp. 686–692.
Juffermans, Nicole P., et al., "Concurrent Upregulation of Urokinase Plasminogen Activator Receptor and CD11b during Tuberculosis and Experimental Endotoxemia", Infection and Immunity, vol. 69, No. 8, 2001, pp. 5182–5185.
Garcia–Monco, Juan Carlos, et al., "Soluble urokinase receptor (uPAR, CD87) is present in serum and cerebrospinal fluid in patients with neurologic diseases", Journal of Neuroimmunology, vol. 129, 2002, pp. 216–223.
Oct. 1, 2002 International Search Report issued during prosecution of PCT/DK02/00341.
Anders Nykjaer et al., "Urokinase Receptor, An Activation Antigen in Human T Lymphocytes," Journal of Immunology, 1994, vol. 152, pp. 505–516.
Cornelia Speth et al., "Urokinase Plasminogen Activator Receptor (uPAR; CD87) Expression on Moncytic Cells and T Cells is Modulated by HIV–1 Infection," Immunobiology, 1998, vol. 199, pp. 152–162.
Satu Mustjoki et al., "Soluble Urokinase Receptor Levels Correlate with Number of Circulating Tumor Cells in Acute Myeloid Leukemia and Decrease Rapidity during Chemotherapy," Cancer Research, Dec. 15, 2000, vol. 60, pp. 7126–7132.
Sun Young Rha et al., "Correlation of tissue and blood plasmingen activation system in breast cancer," Cancer Letters, 2000, vol. 150, pp. 137–145.

* cited by examiner

Primary Examiner—Jeffrey Stucker
(74) Attorney, Agent, or Firm—Darby & Darby

(57) ABSTRACT

Method of diagnosing and/or prognosticating HIV infection in a subject comprising the steps of: (a) performing in vitro a measurement of the level of a marker in the form of (i) urokinase plasminogen activator receptor (uPAR), (ii) soluble urokinase plasminogen activator receptor (suPAR), (iii) urokinase-type plasminogen activator (uPA), (iv) one or more degradation products of (i), (ii), or (iii), and/or (v) an mRNA for (i), (ii) or (iii), in a biological fluid sample from a subject, and (b) using the measurement value obtained to evaluate the state of the subject.

13 Claims, 21 Drawing Sheets

Figure 4: suPAR levels divided into two groups by response to HAART.

Figure 5: Difference in time to AIDS between those with high suPAR and those with low suPAR Figure 6: Difference in survival between those with high suPAR and those with low suPAR Figure 7: No difference in CD4 T cell counts between low suPAR and high suPAR (N=133, p=0.9)

Figure 8: No difference in suPAR between HIV-1 and HIV-2 positives.

Figure 10: suPAR is prognostic for HIV-1 infection

Figure 11: suPAR is prognostic for HIV-2 infection

Figure 12: suPAR levels among HIV negative based on TB diagnosis

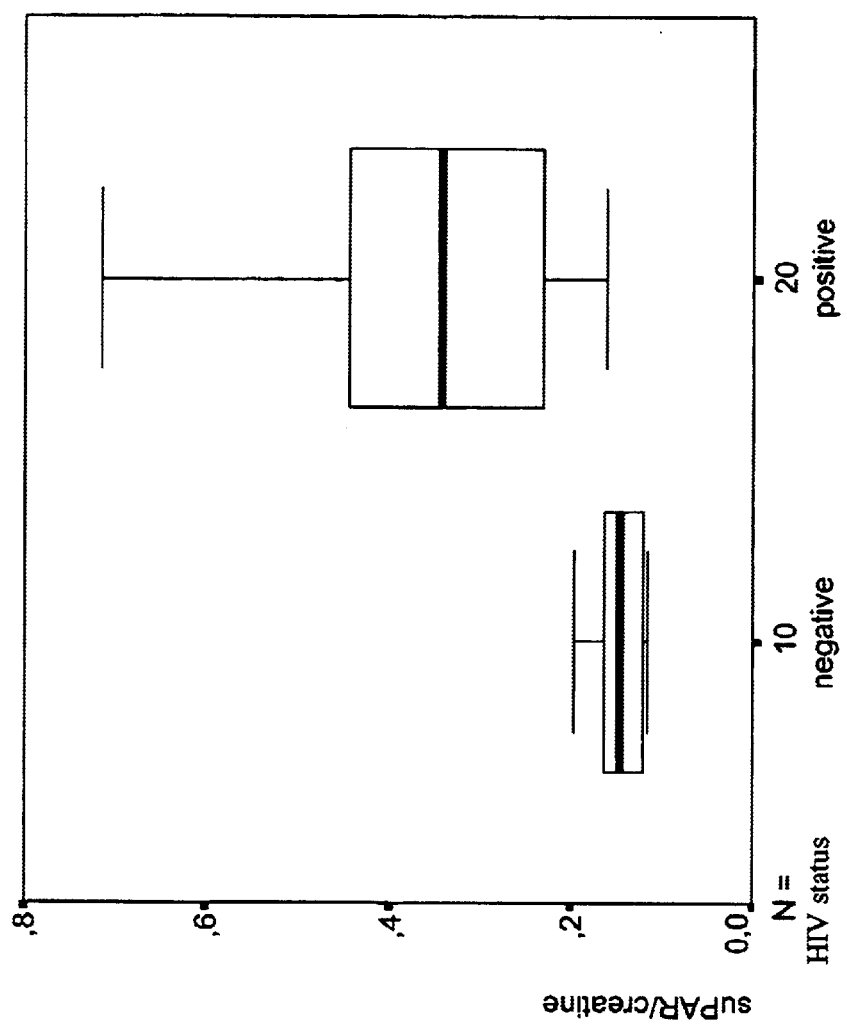
Fig. 17: Urine suPAR/creatinine levels in HIV– and HIV+ (P=0.003)

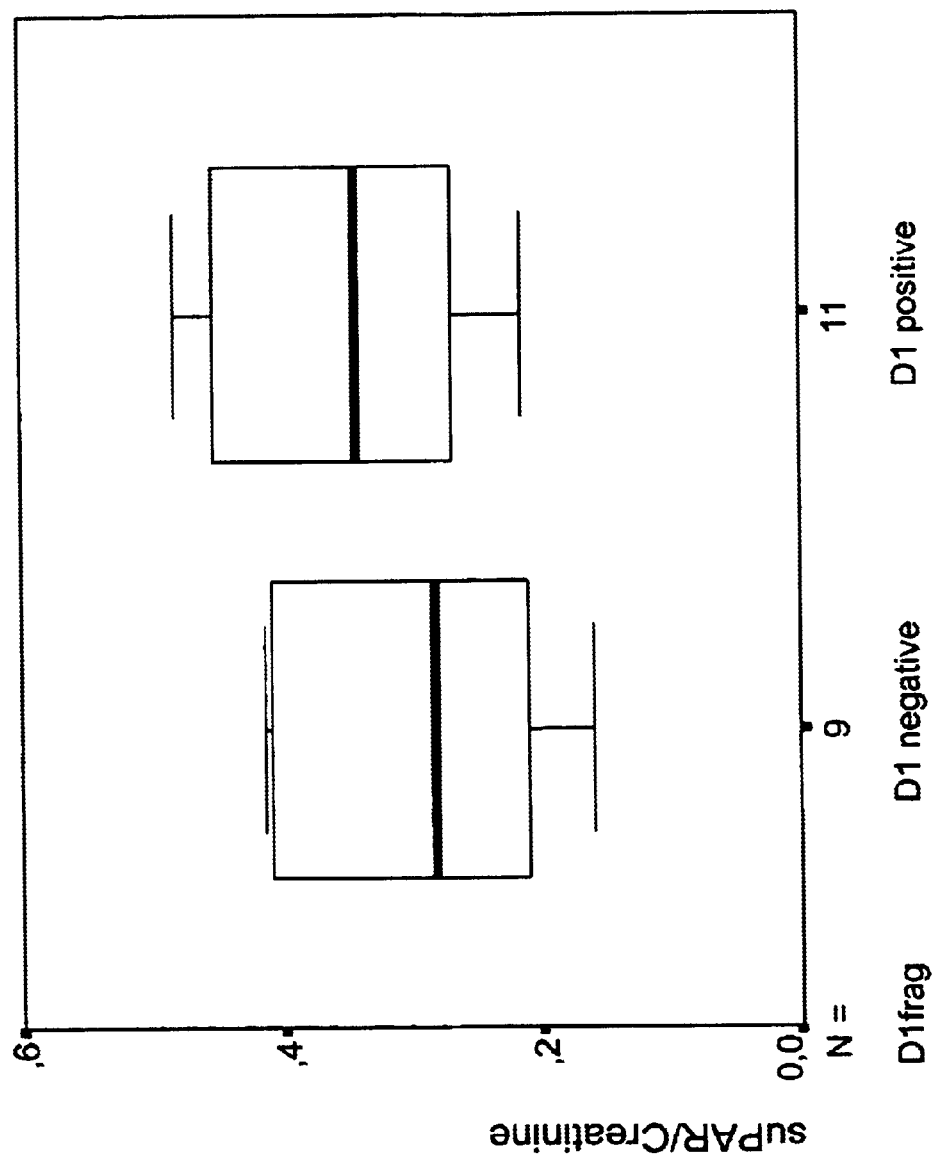
Fig.18: D1 fragments and suPAR

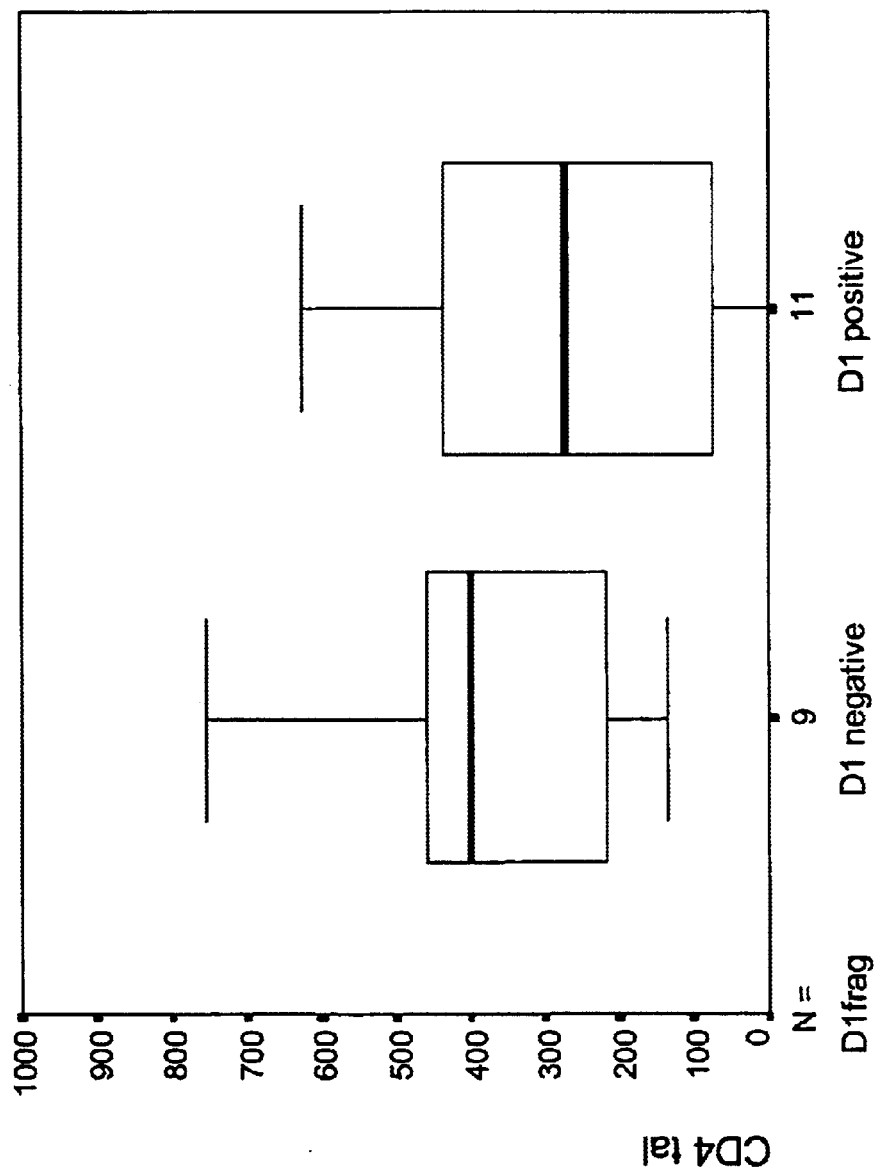
Fig.19: D1 fragments and CD4 counts

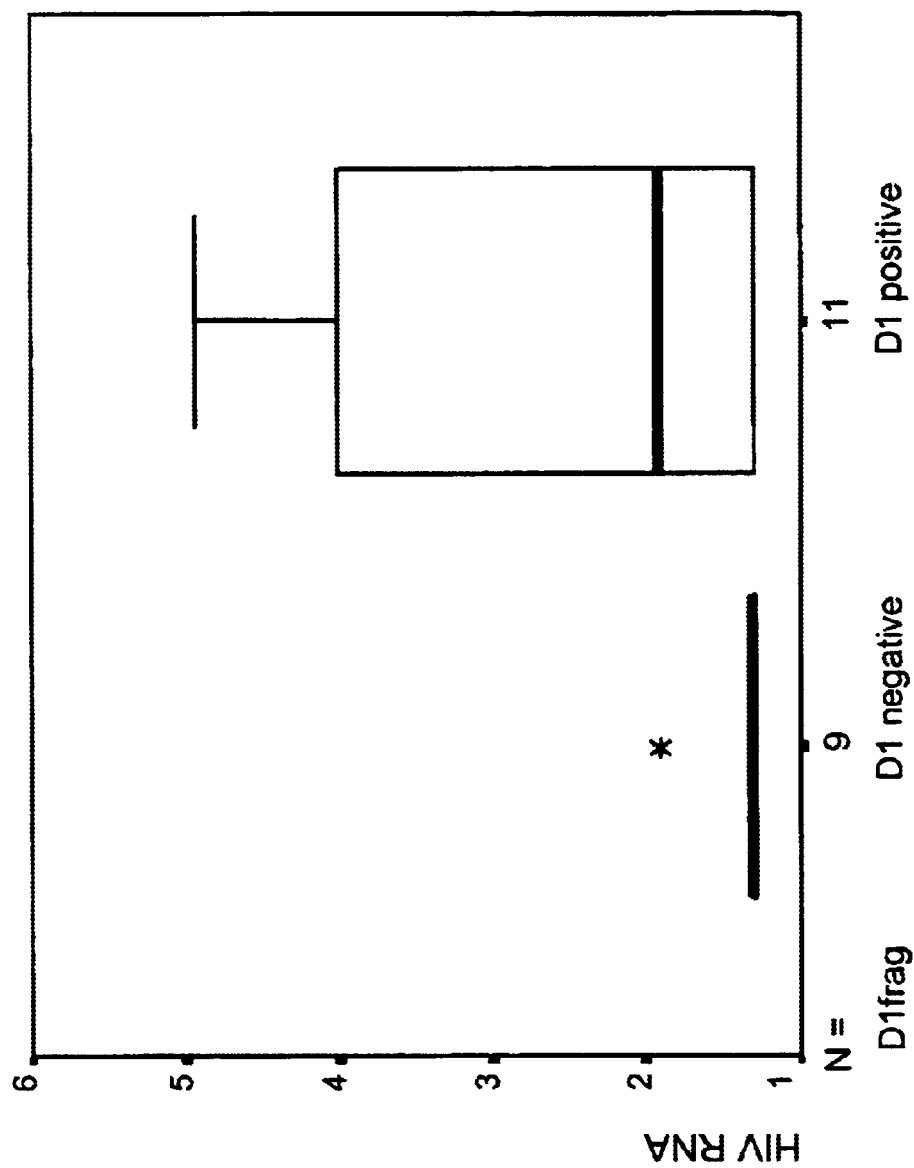
Fig.20: D1 fragments and HIV RNA (Log10 transformed)

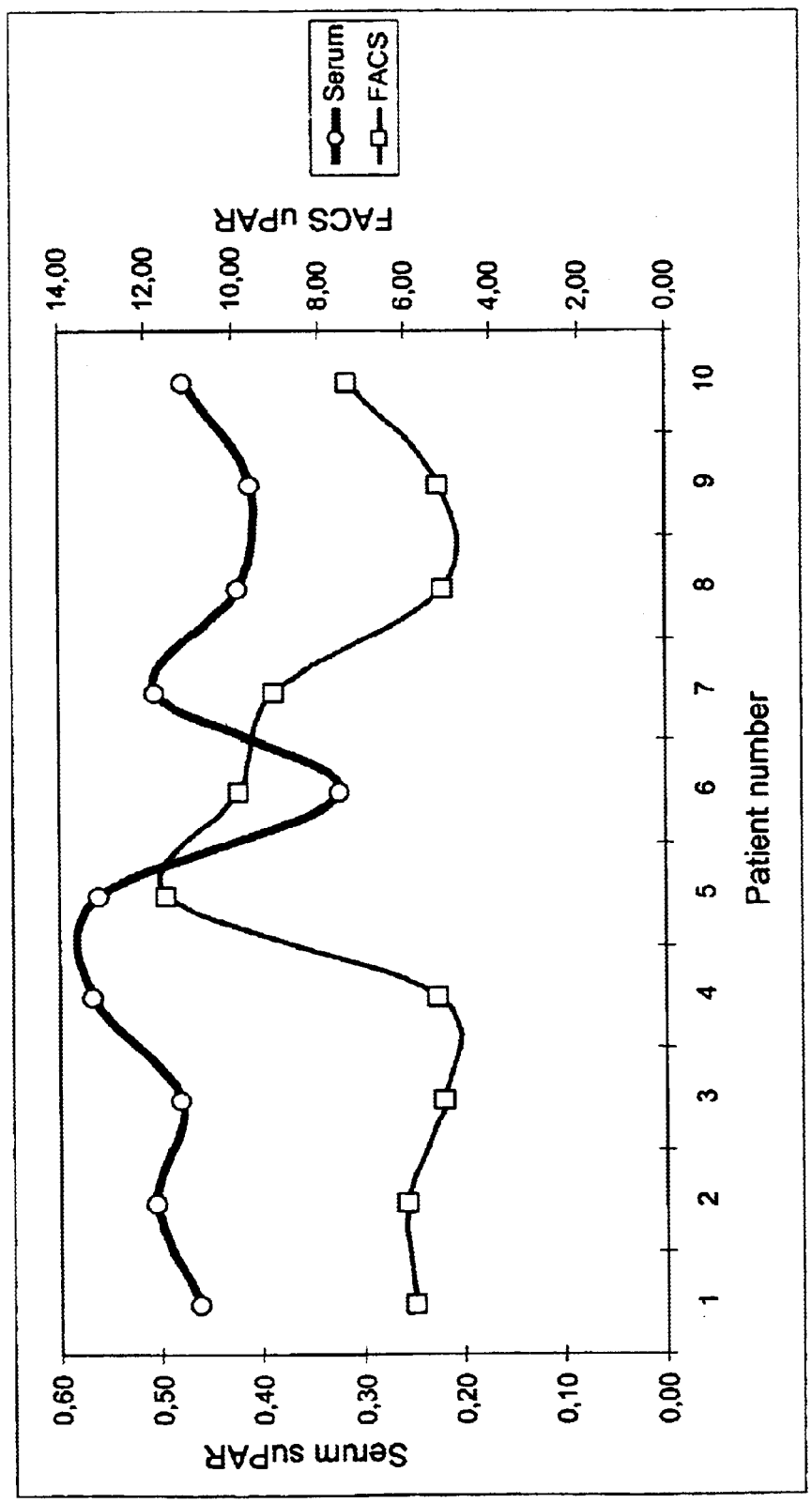
Fig. 21: Correlation between suPAR and uPAR

METHOD AND TOOL FOR PROGNOSTICATING HIV INFECTION IN A SUBJECT BY MEASURING SOLUBLE UROKINASE PLASMINOGEN ACTIVATOR RECEPTOR, DEGRADATION PRODUCTS THEREOF, AND UROKINASE PLASMINOGEN ACTIVATOR RECEPTOR

TECHNICAL FIELD OF THE INVENTION

The present invention concerns the diagnosis and/or prognosis of HIV infection. More particular it concerns the measurements of the concentration of soluble urokinase plasminogen activator receptor (suPAR) in human biological fluids (sputum, cystic fluid, ascites, serum, plasma, urine) as a tool of diagnosing HIV infection as well as the prognosis of disease progression.

BACKGROUND OF THE INVENTION

The cellular receptor for urokinase (uPAR, CD87) plays multiple functions in cell migration, cell adhesion, pericellular proteolysis and tissue remodeling [Blasi, 1997]. uPAR is expressed by most leukocytes including monocytes, macrophages, neutrophils and platelets. uPAR is an activation antigen in monocytes and T cells [Min, 1992][Nykjaer, 1994] and T-cells from HIV-1 infected individuals express elevated levels of uPAR [Nykjaer, 1994]. HIV-1 infection of leukocytes in vitro causes up-regulation of uPAR cell surface expression in a process which appear to be coordinated temporally with the onset of viral replication [Frank, 1996], [Speth, 1998].

uPAR may be shed from the cell surface generating a soluble form of the receptor (suPAR) lacking the GPI-anchor. The shedding mechanism is poorly understood but may occur by GPI-specific phospholipase D catalyzed hydrolytic cleavage of the GPI-anchor (Wilhelm, 1999). Soluble forms of uPAR (suPAR) has been identified in cell culture supernatants and in diverse biological fluids such as tumor ascites, cystic fluid, serum, plasma and recently also in urine [Pedersen, 1993], [Rønne, 1995], [Stephens, 1997], [Sier, 1998], [Chavakis, 1998], [Stephens, 1999], [Wahlberg, 1998], [Sier, 1999].

Serum, plasma and urine levels of suPAR are elevated in patients suffering from different types of cancer [Stephens, 1997], [Sier, 1998], [Stephens, 1999], [Sier, 1998], the paroxysmal nocturnal hemoglobinuria syndrome (PNH) syndrome [Rønne, 1995], [Ninomiya, 1997], and in rheumatoid arthritis patients [Slot, 1999]. The plasma level of suPAR is furthermore a prognostic marker for overall survival in patients suffering from ovarian and colorectal cancer [Sier, 1998], [Stephens, 1999] and for the response to therapy in leukemia [Mustjoki, 1999].

The cellular origin of circulating suPAR is not known. Many, if not all, cells which express uPAR also shed soluble forms of the receptor when cultured in vitro. The source of excess serum suPAR in cancer patients has been suggested to derive from the cancer cells and/or tumor-infiltrating macrophages as these cells often express high levels of uPAR [Stephens, 1997] and experiments using xenografted mice carrying human tumors have indeed demonstrated that the tumor tissue does release suPAR to the circulation and urine [Holst-Hansen, 1999].

Persons infected with HIV-1 probably represents the single most well medically monitored group of patients ever in history. Despite these very intensive studies only few prognostic markers, providing long-term predictions of clinical outcome, have proven strong enough to obtain broad clinical acceptance. Currently used prognostic markers for disease progression in untreated HIV-1 infected patients are essentially restricted to the blood concentration of CD4 positive lymphocytes (the CD4 cell count), the plasma level of HIV-1 RNA (the viral load), and the age of the patient.

CD4+ T cell counting is a general marker of immune deficiency, whereas HIV viral load provides direct information about viral replication. Although these two parameters are based on different approaches, they both provide information about the expected clinical outcome and prognosis of the patient. In specific cases one of the two assays is more useful than the other, which is the reason that both markers are found to be independent parameters in multivariate analysis. Hence, preferably both markers should be used together. Other potential prognostic parameters like age of the patients or β2 microglobulin level give additional information, but usually their significance decrease if they are used in multivariate analyses together with CD4+ or HIV viral load.

After the introduction of highly active anti-retroviral therapy (HAART) therapy, viral load is dramatically reduced and CD4 T cell counts become stable, which decreases the clinical use of these markers for prognostic/diagnostic purposes. Hence, there is a strong need for novel markers useful for monitoring patients in HAART therapy.

Measurements of CD4 cell counts and HIV-1 viral load are expensive and require equipment (flow-cytometers and PCR-machines) which is unlikely to be affordable for wide use in developing countries such as Uganda, Rwanda and Namibia. In these countries, around 30% of individuals between the age of 20 and 49 years are infected (October 1999 data).

SUMMARY OF THE INVENTION

The technical problem addressed by the present invention is to provide a novel marker for diagnosing and prognosticating HIV infection. A further technical problem addressed by the present invention is to provide a marker of the said type, which is simple and affordable to measure.

The present invention has provided a solution to the above technical problems, the invention being directed to a method of diagnosing or prognosticating HIV infection in a subject comprising the steps of (a) performing in vitro a measurement of the level of a marker in the form of (i) urokinase plasminogen activator receptor (uPAR), (ii) soluble urokinase plasminogen activator receptor (suPAR), (iii) urokinase-type plasminogen activator (uPA), (iv) one or more degradation products of (i), (ii) or (iii), and/or (v) an mRNA for (i), (ii) or (iii), in a biological fluid sample from a subject, and (b) using the measurement value obtained to evaluate the state of the subject.

The invention is based on the discovery that soluble uPAR (suPAR) is present in elevated levels in serum, plasma and urine of HIV infected individuals, and that the level of suPAR is useful as a diagnostic marker. Also, the level of suPAR in HIV infected individuals is prognostic for the development of AIDS, the CD4 T cell decline, and death. The suPAR level is a novel and highly diagnostic and prognostic factor, even in the context of other known prognostic factors related to HIV disease. In fact, in various multivariate analyses including all presently known relevant survival-related parameters, suPAR was the second strongest parameter after CD4 T-cell count. In a comparative analysis against CD4, suPAR kept its highly significant prognostic value (Hazard Rate (HR) 2.5, P<0.001), whereas the other markers became less significantly associated with survival.

Moreover, the present invention is based on the discovery that, at least for some HIV patients, not only was the total suPAR level enhanced, but there was also a change in the ratio between various degradation product variants of suPAR. The pattern of these variants was clearly different in some subgroups of patients compared to healthy blood donors. Therefore, the measurement of one or more degradation product variants of suPAR may also be used as a marker for diagnosing and prognosticating HIV infection.

Furthermore, the present invention is based on the recognition that the amount of suPAR is correlated to the amount of uPAR as well as to the amount of uPA, and that therefore the amounts of uPAR and uPA are equally suitable as diagnostic and prognostic indicators of HIV infection.

Finally, when uPAR, suPAR and uPA are present at high levels, i.e. expressed at high levels, this means that mRNA for the said proteins are present at high levels, and therefore said mRNA are equally suitable as diagnostic and prognostic indicators of HIV infection.

A further advantage of the invention is that measurement of suPAR can be performed using e.g. a simple ELISA technique or even a stick and may therefore provide a very inexpensive, simple and quick supplement to the currently used prognostic tools for HIV-1 infected persons. Thus, in developing countries without the financial possibility to carry out the costly assays used in the western world, suPAR levels could be used 1) to determine HIV status (diagnosis), 2) to select patients for treatment (prognosis), and 3) to monitor the progress of treatment.

Furthermore, the present invention involves the advantage that while suPAR levels also can be measured in a urine sample, a blood sample is necessary for measurement of CD4 counts and HIV viral load, and of course a urine sample is much more easy to obtain.

The invention further relates to a method of evaluating the progression of the state of a subject suffering from HIV infection comprising the steps of (a) performing in vitro a measurement of the level of a marker in the form of (i) urokinase plasminogen activator receptor (uPAR), (ii) soluble urokinase plasminogen activator receptor (suPAR), (iii) urokinase-type plasminogen activator (uPA), (iv) one or more degradation products of (i), (ii) or (iii), and/or (v) an mRNA for (i), (ii) or (iii), in each of a number of biological fluid samples from a subject, wherein the samples are obtained at different points in time, and (b) using the measurement values obtained to evaluate the progression of the state of the subject.

This method may be used to continuously monitor the state of the patient.

Finally, the present invention relates to an ELISA-kit according to claim 8, and a stick-kit according to claim 9.

BRIEF DESCRIPTION OF DRAWINGS

FIG. 17 is a chart of the level of suPAR for HIV negative and positive patients.

FIG. 18 is a chart of the CD4 T cell count for D1 fragment negative and positive patients.

FIG. 19 is a chart of the suPAR level for D1 fragment negative and positive patients.

FIG. 20 is a chart of HIV mRNA level for D1 negative and positive patients.

FIG. 21 is a chart showing the correlation between the suPAR level and the uPAR level.

DETAILED DESCRIPTION OF THE INVENTION

In the following, the invention is explained in particular with reference to suPAR for reasons of simplicity. This should not be understood as a limitation of the scope of the present invention to suPAR. Furthermore, suitable extrapolations to uPAR, uPA and the degradation products of all the said three substances lie well within the skill of a person skilled in the art.

Figure 3:
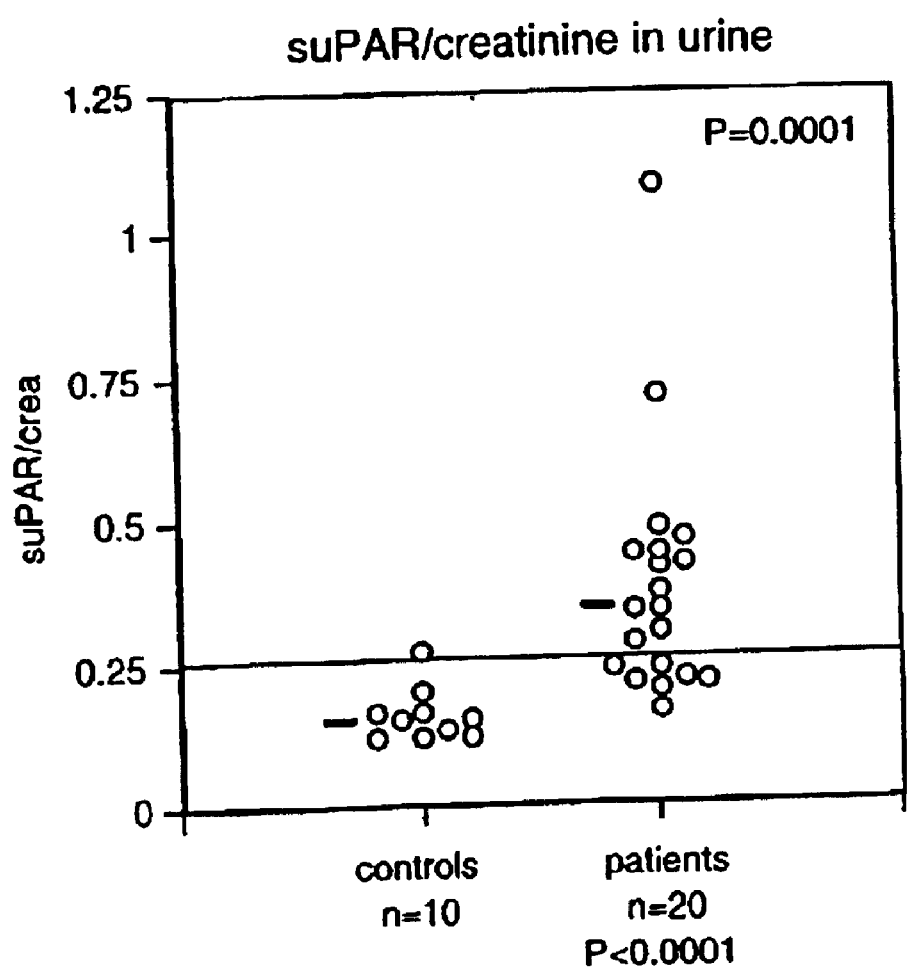
FIG. 3 shows the concentration of suPAR/creatinine in urine for a group of HIV-negative volunteers and for a group of patients in HAART therapy.

The inventors have surprisingly found that the concentration of suPAR, a molecule that is in general known to be involved in cell migration and adhesion, is increased in serum and urine from HIV-infected persons compared with healthy controls. Enhanced serum suPAR levels detected 91.6% of the HIV-patients (n=191) with a specificity of 93.3%, cf. Example 1. Moreover, subgroups of patients with low, intermediate and high levels of suPAR, respectively, showed significant differences in survival, cf. Example 2. Patients in the intermediate suPAR group had an enhanced hazard ratio (HR) of 2.17, whereas high suPAR serum levels were even more hazardous (HR 3.29, see Table 1 below). The prognostic value of suPAR stayed significant even when it was tested in a multivariate analysis against the strongest known parameters presently available. In fact, suPAR was found to be the second strongest prognostic factor, directly after CD4+ C-cell counts, and even in a direct comparison with CD4 (or any of the other parameters) suPAR kept its independent prognostic value (P<0.001). These results suggest that the serum levels of suPAR alone (preferably in combination with CD4+ and HIV-viral load) could be a strong clinical tool for the diagnosis/prognosis of HIV-patients. The same is true for urinary suPAR values as indicated in FIG. 3. Also, analysis of the fragmentation of suPAR in body fluids provides additional information.

The biological fluid sample may be any fluid that can be obtained from humans i.e. sputum, cystic fluid, ascites, blood, serum, plasma, and urine. Urine is preferred due to the fact that it is easy to obtain. When urine is used as the biological fluid sample, the measurement of the marker should be correlated to the total concentration level of the sample, e.g. by correlating the measurement of the marker to the content of creatinine in the sample.

Preferably, the biological fluid sample is stored at a temperature of below 0° C., more preferably from −20° C. to −80° C., until measurement.

The measurement of the marker in the biological fluid sample may be carried out using any available method/device therefore. Examples of such measurement methods/devices are ELISA, RIA (radioimmunoassay), western blotting, FACS analysis, sticks, etc. Also, measurement may be carried out by determining mRNA expression using RT-PCR, northern blotting, RNase protection assay or using micro-array techniques etc. Preferred measurement methods/devices are ELISA and sticks.

An ELISA may be carried out in a number of different embodiments, many of which are applicable in the present invention. One ELISA embodiment, which is particularly suitable for use in the present invention, is the one described by [Holst-Hansen, 1999] and [Stephens, 1999], which are included herein by this reference.

The measurement of the marker may be carried out using any suitable stick. Preferably, the stick is a stick comprising an antibody to the marker as a capture agent.

Preferably, the measurement of uPAR or uPA in the biological fluid sample is carried out by FACS analysis, western blotting or ELISA. mRNA levels may be determined using RT-PCR, Northern blotting, Micro arrays or protection assays.

Preferably, the measurement of uPAR/suPAR/uPA degradation products is carried out using western blotting.

The measurement of uPAR is carried out in biological fluid samples containing uPAR expressing cells, i.e. blood samples.

The measurement value of the level of marker obtained in step (a) may be used to evaluate the state of the subject by comparing the measurement value with the level of the marker in subjects not infected with HIV virus.

As mentioned above, one aspect of the present invention relates to a method of evaluating the progression of the state of a subject suffering from HIV infection. In particular, this method is suitable for monitoring subjects undergoing treatment, e.g. highly active anti-retroviral therapy (HAART).

The measurement values of the level of marker obtained in step (a) may be used to evaluate the progression of the state of the subject by comparing the measurement values with the level of the marker in subjects not infected with HIV and/or by comparing the temporal course of measurement values with that of subjects not infected with HIV.

The invention further relates to an ELISA-kit for evaluating the physical state of a subject suffering from HIV infection comprising a) an immobilised capture agent capable of capturing a marker in the form of (i) urokinase plasminogen activator receptor (uPAR), (ii) soluble urokinase plasminogen activator receptor (suPAR), (iii) urokinase-type plasminogen activator (uPA), (iv) one or more degradation products of (i), (ii) or (iii), and/or (v) an mRNA for (i), (ii) or (iii), and b) a binding partner capable of binding to the marker, the binding partner comprising c) a label system.

The capture agent may be an antibody to the marker.

The binding partner may be an antibody to the marker.

Preferably, the label system is conjugated to the binding partner. The label system may be any conventionally used label system, such as antibody to the binding agent conjugated to an enzyme, e.g. an immunoglobulin-alkaline phosphatase conjugate.

Furthermore, the invention relates to a stick for evaluating the physical state of a subject suffering from HIV infection comprising a) an immobilised capture agent capable of capturing a marker in the form of (i) urokinase plasminogen activator receptor (uPAR), (ii) soluble urokinase plasminogen activator receptor (suPAR), (iii) urokinase-type plasminogen activator (uPA), (iv) one or more degradation products of (i), (ii) or (iii), and/or (v) an mRNA for (i), (ii) or (iii), and b) a binding partner capable of binding to the said marker, the binding partner comprising c) a label system.

The capture agent may be an antibody to the marker.

The binding partner may be an antibody to the marker.

Preferably, the label system is conjugated to the binding partner. The label system may be any conventionally used label system, such as antibody to the binding agent conjugated to an enzyme, e.g. an immunoglobulin-alkaline phosphatase conjugate.

Definitions

In connection with the present invention, "HIV" is defined as Human Immunodeficiency virus 1 and 2.

In connection with the present invention 'uPAR' is defined as any form of uPAR (same as CD87) present on the surface of uPAR expressing cells in biological fluids.

The expression "uPAR expressing cells" refers to all cells expressing uPAR (CD87) such as monocytes, leucocytes, macrophages, and nieutrophiles.

In connection with the present invention "suPAR" (soluble uPAR) is defined as any form of uPAR (same as CD87) present in biological fluids in a non-cell-bound form.

In connection with the present invention "uPA" is defined as the total of any form of uPA present in biological fluids, i.e. both uPA bound to cells via uPAR and soluble uPA.

"Biological fluids" are defined as any fluid that can be obtained from humans i.e. sputum, cystic fluid, ascites, blood, serum, plasma, and urine.

The expression "degradation product of suPAR, uPAR and uPA" as used herein means all fragments thereof observed using western blotting or antibodies against suPAR, uPAR or uPA, respectively. In particular, the said expression includes the D1, D2 and D3 fragments of suPAR.

EXAMPLES

Example 1

Diagnosis of HIV Infection by Measurement of Serum suPAR

Aim:

To determine whether HIV patients has elevated levels of suPAR in serum, i.e. whether suPAR levels may be used to diagnose HIV infection.

Description of the Experiment:

Using ELISA, the concentration and fragmentation of suPAR in serum samples from healthy donors and from HIV-infected patients were measured.

suPAR was measured retrospectively on thawed serum samples by ELISA as described by [Holst-Hansen, 1999] and [Stephens, 1999]. The following minor modifications of the technique were used: BSA was used as a blocking reagent in stead of SuperBlock (Pierce Biochemicals), and endpoint measurements were used in stead of kinetics. These modifications were not found to affect the sensitivity and/or specificity of the assay notably.

Figure 1:
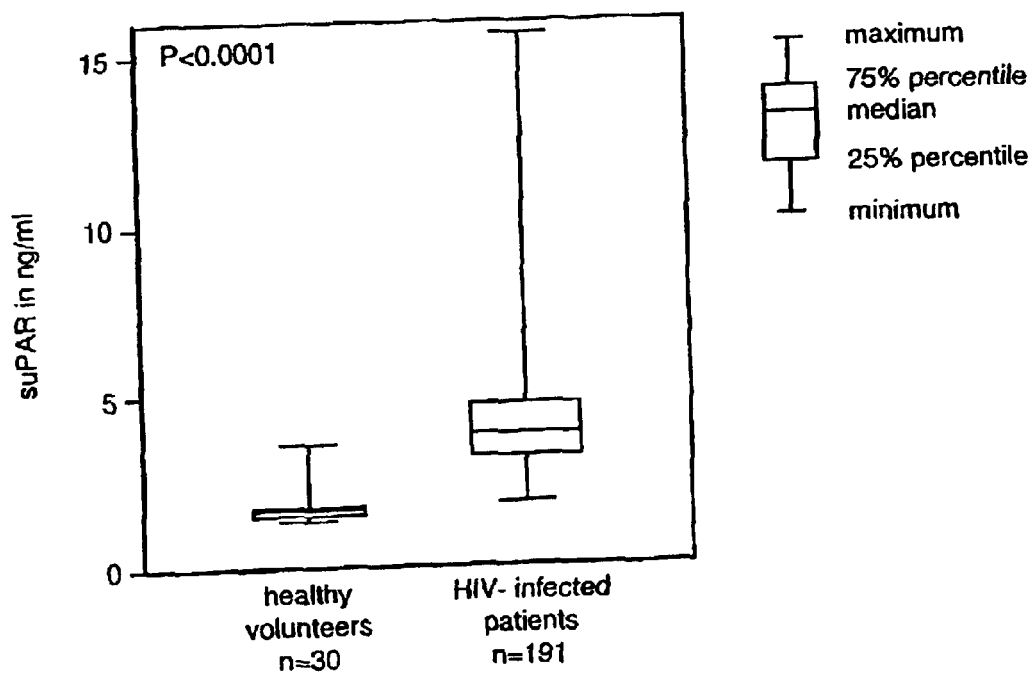
FIG. 1 shows a so-called Box-whisker plot of the concentration of suPAR for a group of healthy blood donors and for a group of HIV-positive individuals.

Results:

The results obtained are shown in FIG. 1, which is a Box-whisker plot showing elevated concentrations of suPAR in serum from 191 HIV-positive individuals compared to healthy blood donors. The difference is highly significant according to the Mann-Whitney U-test (P<0.0001). High levels of suPAR (higher than the mean plus 2 times the standard deviation of the suPAR level in healthy donors) were found in 91.6% of the patients, whereas only 6.3% of the healthy donors showed enhanced levels.

High serum concentrations of suPAR (cut-off value: 2.61 ng/ml=mean level in blood donors+2×S.D.) were strongly indicative of HIV infection with 91.6% sensitivity and 93.3% specificity. Survival analyses showed that next to the diagnostic value enhanced suPAR serum levels were also highly indicative for survival of the patients.

Discussion:

The experiment suggests that patients could be diagnosed/screened for HIV-infection in a cheap and convenient way by using ELISA on serum. This could be of use particularly in low developed countries, where costs, easy handling and low hazardness are more relevant.

Example 2

Prognosis of HIV Infection by Measurement of Serum suPAR

Description of the Experiment:

The results obtained in Example 1 were used to perform a Kaplan-Meier survival analysis of 191 HIV-positive patients. The patients were divided in 3 equal groups (tertiles, n=63, n=64 and n=64 respectively) based on suPAR concentrations in serum. The overall difference between the groups was highly significant according to the log-rank test (P<0.0001).

Figure 2:
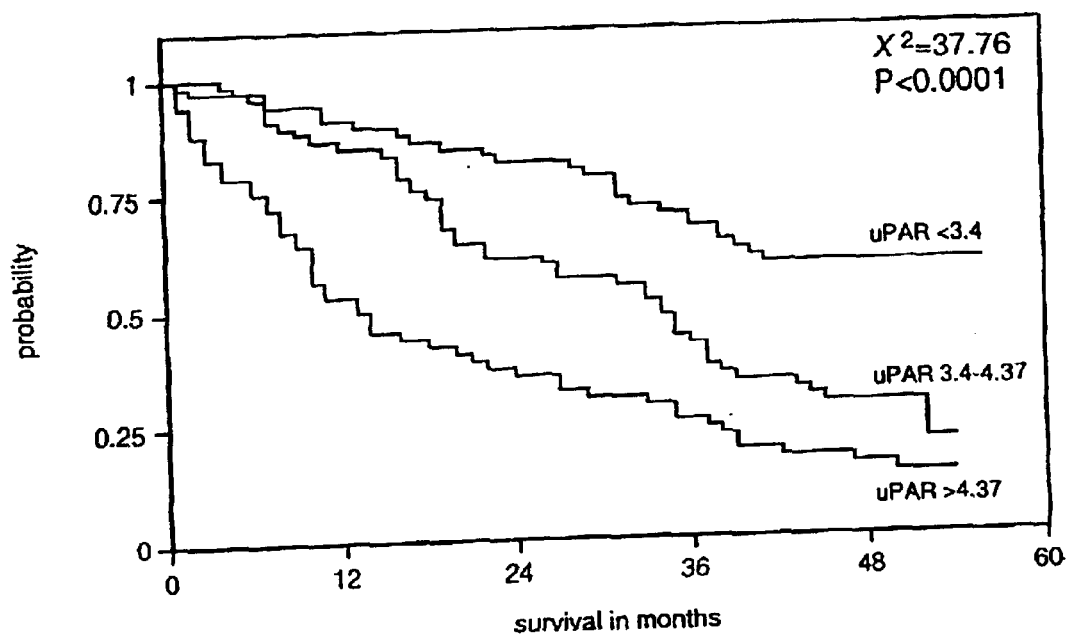
FIG. 2 shows a so-called Kaplan-Meier survival analysis plotting the probability of survival versus time in months for 191 HIV-positive patients divided into 3 groups based on suPAR concentrations in serum.

Results:

The results are presented in FIG. 2 and in Table 1 below.

|  | univariate | | | multivariate | | |
| --- | --- | --- | --- | --- | --- | --- |
|  | HR | P | CI | HR | P | CI |
| age | 1.36 | ns | 0.88–2.10 | 1.37 | ns | 0.72–2.60 |
|  | 1.48 | ns | 0.98–2.24 | 1.92 | 0.038 | 1.04–3.54 |
| CD4+ | 4.52 | <0.001 | 2.57–7.94 | 3.89 | <0.001 | 2.01–7.33 |
|  | 14.79 | <0.001 | 8.39–26.07 | 12.18 | <0.001 | 5.76–25.76 |
| β2-micro- | 2.03 | 0.004 | 1.25–3.30 | 1.12 | ns | 0.60–2.11 |
| globulin | 4.83 | <0.001 | 3.00–7.78 | 1.73 | ns | 0.87–3.43 |
| HIV-load | 2.48 | 0.003 | 1.38–4.47 | 2.77 | 0.002 | 1.44–5.34 |
|  | 5.22 | <0.001 | 2.95–9.26 | 2.90 | 0.004 | 1.41–5.95 |
| suPAR | 2.17 | <0.001 | 1.40–3.36 | 2.91 | <0.001 | 1.59–5.33 |
|  | 3.29 | <0.001 | 2.11–5.14 | 3.50 | <0.001 | 1.80–6.81 |

Table 1 gives the results of Cox proportional hazards survival analyses on 'tertiled' parameters showing the prognostic value of serum suPAR levels alone and in comparison with other known prognostic factors in a group of 191 HIV patients. All parameters were treated as tertiles corresponding to FIG. 2. As expected most of the parameters lost some of their significance in the multivariate analyses compared to the univariate counterpart, in particular age and β2-microglobulin, but CD4+ and especially suPAR kept their significance completely. The multivariate analyses included 138 patients.

HR: hazard ratio; CI: confidence interval; ns: not significant.

Discussion:

The height of the suPAR level has strong prognostic value independent from the most relevant other markers CD4+ T-cell count and HIV-load. suPAR levels are not correlated with HIV-load and only weakly with CD4+ (R=0.303) and is an independent parameter in multivariate survival analysis, indicating that suPAR gives additional information for prognosis. This implicates that suPAR could especially be useful in circumstances that these other markers are not usable, for instance for monitoring patients during HAART-therapy.

Example 3

Prognosis of HIV Infection in HAART Patients by Measurement of Urinary suPAR

Aim:

To determine whether HAART patients have elevated suPAR levels compared with HIV negative controls. If so, suPAR may hold prognostic value in HAART patients in whom viral load is no longer measurable (and therefore has no prognostic value) and CD4 T cell counts remain steady (and therefore has no prognostic value).

Description of the Experiment:

Twenty HIV patients without AIDS undergoing HAART therapy kindly donated urine. Furthermore, 10 HIV negative hospital workers donated urine. Creatinine and suPAR was measured in the urine samples and is expressed as suPAR/creatinine. The HAART patients had a significant higher level of suPAR/creatinine compared to healthy controls (FIG. 3).

Results

The results obtained are shown in FIG. 3, which shows elevated concentrations of suPAR in urine obtained from patients in HAART therapy compared with urinary suPAR levels from HIV-negative volunteers. suPAR was normalized for urine dilution by the creatinine concentration. The difference between both groups was highly significant according to Mann Whitney U-test (P<0.0001).

Discussion:

Patients receiving HAART therapy have elevated levels of suPAR. This may be used to monitor the success of therapy, such as to predict viral rebounce in patients undergoing HAART therapy.

Example 4

The suPAR Level is Predictive for the Decrease in CD4 T Cell Counts in HIV Infected Individuals Introduction In Example 2 and 3 it was shown that suPAR is a strong prognostic factor. In the Copenhagen HIV Immune Cohort (CHIC), cf. ref. 18–25, it was further shown that various factors are prognostic to the progression to death.

In this Example it is investigated whether various prognostic factors can predict CD4 T cell decline.

Materials and Methods:

Random coefficient regression models were used to analyse the relationship between individual CD4 counts during 1-year follow-up after the first measurement on one side and possible explanatory variables on the other side. CD4 counts were used as dependent variables on a natural log scale assuming an individual linear development during the one-year of follow-up. LogCD4=time (in years)+time*log HIV RNA+time*age (in years) was used as an initial basic model calculating the individual development in CD4 count as a function of individual viral load and individual age. This model calculates a basic slope and estimates the effect on the CD4 count slope added by viral load and age. The following additional independent variables were added to the model one by one, to calculate if any of these variables had any significant effect on the CD4 count slope once viral load and age were known: Beta2-microglobulin, IgA (immunoglobulin A), IFN-gamma (interferon-gamma), MIP-1 (macrophage inflammatory protein), suPAR, LAK (leucocyte activated killer) cell activity, TTV (TT virus) titer. Any effect on the slope of the CD4 curve by antiretroviral treatment at enrolment or by initiation of antiretroviral treatment during the one-year follow-up was also evaluated.

Results

The results obtained in CHIC were used as a basis for the calculations in the present Example. The results appear e.g. from references 18–25.

When added to the original model with age and viral load, suPAR was the only variable that showed any significant correlation with the CD4 T cell decline. In this model 1 ng/ml higher suPAR corresponds to 0.11 decrease in log (CD4). In comparison, 1 log10 higher plasma HIV RNA corresponds to 0.48 decrease in logCD4 whereas 1 year older age corresponds to 0.02 decrease in logCD4 during one year of follow-up.

On a linear scale these figures translates to a 10.4%, 38.2% and 2.0% annual decrease in CD4 count per: 1 ng/ml higher suPAR, 1 log10 higher plasma HIV RNA, and 1 year older age, respectively. These numbers translate into a 79.5% higher loss of CD4 cells in average for the patient with the highest suPAR level (15.5 ng/ml) compared to the patient with the lowest level.

Discussion

The CHIC cohort is one of the most studied cohorts in the world with respect to prognostic factors (ref. 18–25). The CD4 T cell counts, HIV viral load, Beta-2-microglobulin, IgA, IFN-gamma, MIP-1-beta, suPAR, LAK cell activity, age and TT viral load have been shown to carry prognostic value for progression to death. In this study, we investigated whether any of these prognostic factors could predict the CD4 T cell decline. The random coefficient regression model showed that only the age of the patient, the HIV viral load and the serum level of suPAR are significantly associated with the CD4 T cell decline.

Example 5

SuPAR can Predict Outcome of Therapy in HIV Infected Individuals

Introduction

Approximately half of the patients who start in Highly Active Anti-Retroviral Therapy (HAART) experience viral rebound after six months of treatment. In this Example it is investigated whether serum suPAR is reduced during HAART and whether the pre-HAART suPAR value is predictive for the potential efficacy of treatment.

Materials and Methods:

Thirty-three HIV positive patients from Department of Infectious Diseases, Hvidovre University Hospital, were included in the study. Sixteen patients had undetectable viral RNA six months after HAART initiation and seventeen patients had detectable viral RNA after 6 months of HAART (>200 copies/ml). Twenty-eight patients had been subjected to antiretroviral treatment prior to the start of HAART and five patients had not been exposed to treatment previously.

Five samples were obtained from each patient, two samples preceeding HAART and three samples after initiation of HAART. The samples were named S1 to S5. S1 was obtained median 3.9 months preceding HAART (range: 1.1–106.6 months), S2 was obtained median 0.6 months preceeding HAART (range: 0.3–5.7 months), S3 was obtained median 1.9 months after initiation of HAART (range: 0.7–8.6 months), S4 was obtained median 6.4 months after initiation of HAART (range: 1.8–16.1 months), S5 was obtained median 21.4 months after initiation of HAART (range: 5.7–39.6 months). CD4 counts were obtained by routine FACS analysis. HIV viral load was determined using Roche Amplicor HIV RNA kit according to the manufactures instructions. SuPAR was measured using ELISA with R2 as catching antibody and polyclonal rabbit Alfa-uPAR as detecting antibody. The ELISA was carried out as in reference 26.

Results:

After HAART (S5), the suPAR level had dropped compared to the last sample before HAART initiation (S2) with an average of 15%.

Figure 4:
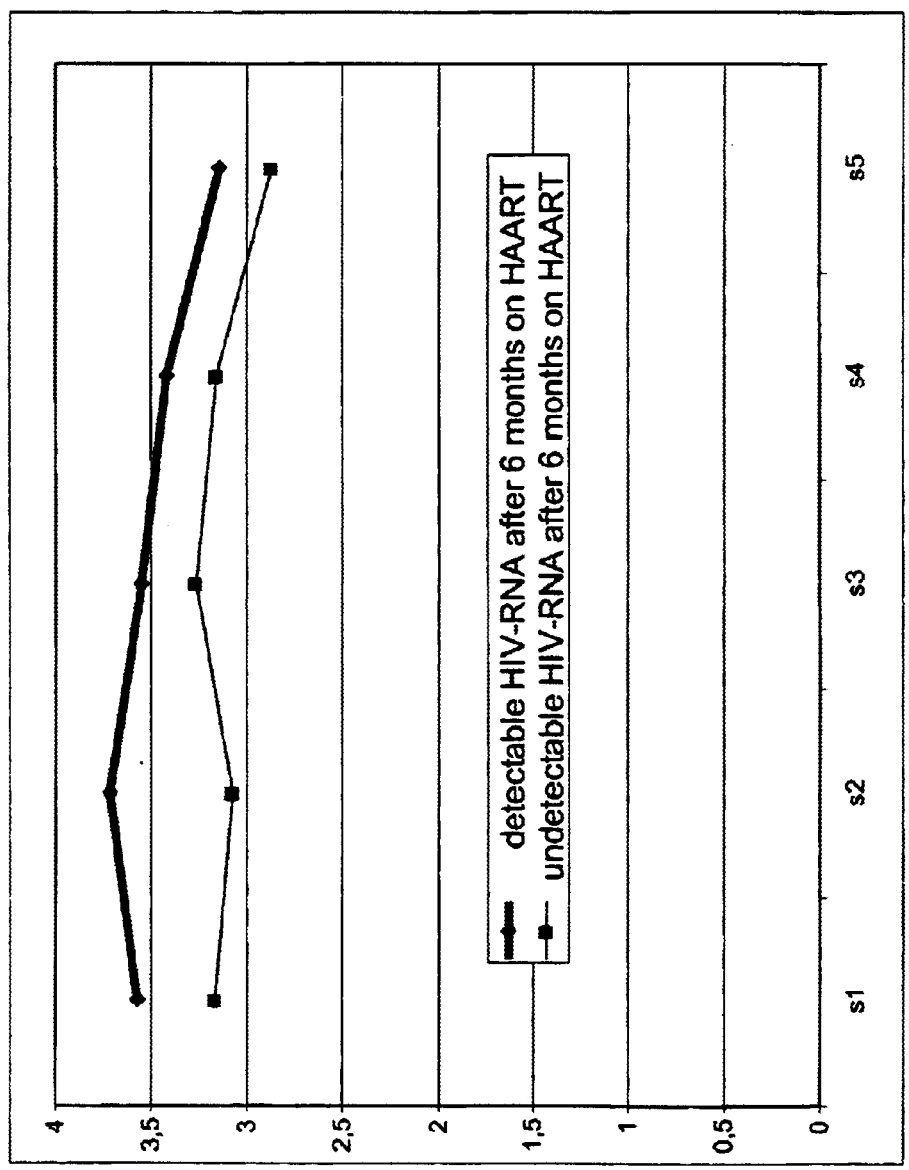
FIG. 4 shows the suPAR levels for two groups of patients during HAART in a Mann-Whitney U-test (p=0.05).

Those who failed therapy (experienced viral rebound after 6 months of treatment) had higher suPAR levels both before and after HAART. The suPAR value in the last sample before HAART initiation (S2) contained higher levels of suPAR in those patients that had viral rebound after HAART. FIG. 4 shows the suPAR levels divided into two groups by response to HAART for S1–S6 in a Mann-Whitney U-test; p=0.05.

Discussion:

This study comprised 33 patients, who were followed before and after initiation of therapy. The patients were selected on whether they had a good or bad response to treatment, as determined by whether they experienced viral rebound after six months of treatment. Even though the number of patients in this study was small, it was found that those patients who experienced viral rebound had significantly higher levels of suPAR in the serum samples taken before treatment compared to those patients whose HIV viral load remained fully suppressed after six months of HAART. Even though these data have to be confirmed in larger studies, these data strongly indicate that suPAR carry important information on the outcome of HAART.

Example 6

The suPAR Level in Serum Increases During HIV Infection and is Prognostic for Survival Fifteen haemophilic HIV positive patients were followed up to 17 years after the first HIV positive test. The serum suPAR level and the CD4 T cell count were measured. During the follow-up, 8 patients died. The serum suPAR level significantly increased during infection, and both the increase as well as the suPAR level was significantly associated with survival. When performing a Cox univariate analysis, both the first CD4 T cell count and the first suPAR level were significantly associated with survival. Both remained significantly associated with survival when included in a multivariate Cox regression model. Furthermore, the suPAR level was predictive for the CD4 T cell decrease over time.

Example 7

The Serum Level of Soluble uPAR is Prognostic for Development of AIDS and Death in HIV Infection Introduction In Examples 2–6 it was shown that the soluble form of the urokinase plasminogen activator receptor (suPAR) is a strong and independent prognostic factor for HIV disease progression. In this example, the strong prognostic value of suPAR is confirmed in another Danish cohort. Furthermore, the possible prognostic value of PAI-1 4G/5G promoter polymorphism is investigated.

Recently, the prognostic value of suPAR in the Copenhagen HIV Immune Cohort (CHIC) (26) was investigated. It was found that the serum level of suPAR was a strong prognostic marker in this Danish cohort. Furthermore, the prognostic strength was independent of the CD4 T cell count and the HIV RNA.

The reason for the strong prognostic value of suPAR is not known. It has previously been demonstrated that uPA binds to the conserved apex sequence -GPGR(A/V)- of the V3-loop in gp120 (27), a sequence very important for viral function and implicated in the binding to chemokine receptors. Thus, it is likely that uPA may form a bridge between uPAR located on the cell surface and HIV. If this is the case, uPA carries prognostic value. Also, PAI-1 which may bind and internalise uPA/uPAR complexes (28) and the amount of PAI may therefore have an effect of the number of available uPA/uPAR complexes. The 4G/5G genetic polymorphism in the PAI-1 promoter has been shown to influence the plasma PAI-1 level (29). Thus, in this example, different components of the plasminogen activator system and their possible prognostic value in a Danish cohort of HIV infected homosexual men have been investigated.

Subjects and Samples

All subjects are part of the Copenhagen AIDS cohort (CAC). The cohort is a seroprevalent cohort established between 1984 and 1988, with the majority (81%) of the 153 subjects enrolled in 1985 (30). All subjects were homosexual Danish men. At enrollment a thorough physical examination was performed, and blood was drawn. The CD4 counts used in this study correspond to the time of serum sample. Informed consent was obtained from all participants. The cohort was approved by The Medical Ethics Committee of Copenhagen County. AIDS was diagnosed in accordance with the 1987 Centers for Disease Control and Prevention criteria (AIDS-87). Eight patients had developed AIDS at the time of serum sampling. Of the 133 patients from whom serum was available, 89 patients died during the follow-up. Of these, eight died for unknown reasons without having been diagnosed with AIDS. DNA was available from 113 of the patients for the PAI-1 promoter analysis.

SuPAR Measurement

SuPAR was measured as previously described (9).

Statistics

Survival analysis and analysis of time to development of AIDS were made using Cox regression analysis and Kaplan Meier analysis. Comparisons between groups were made with Student's test.

Figure 5:
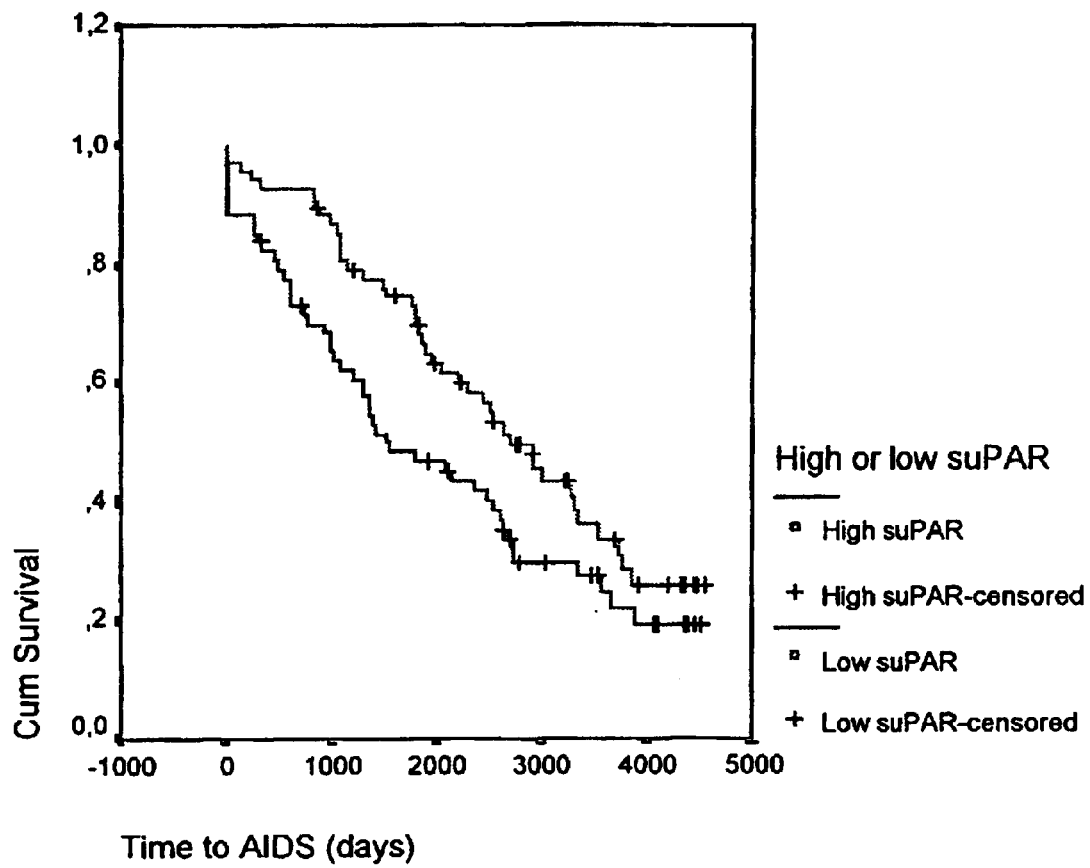
FIG. 5 is a plot of the time to start of AIDS for high and low suPAR level patients.
Figure 6:
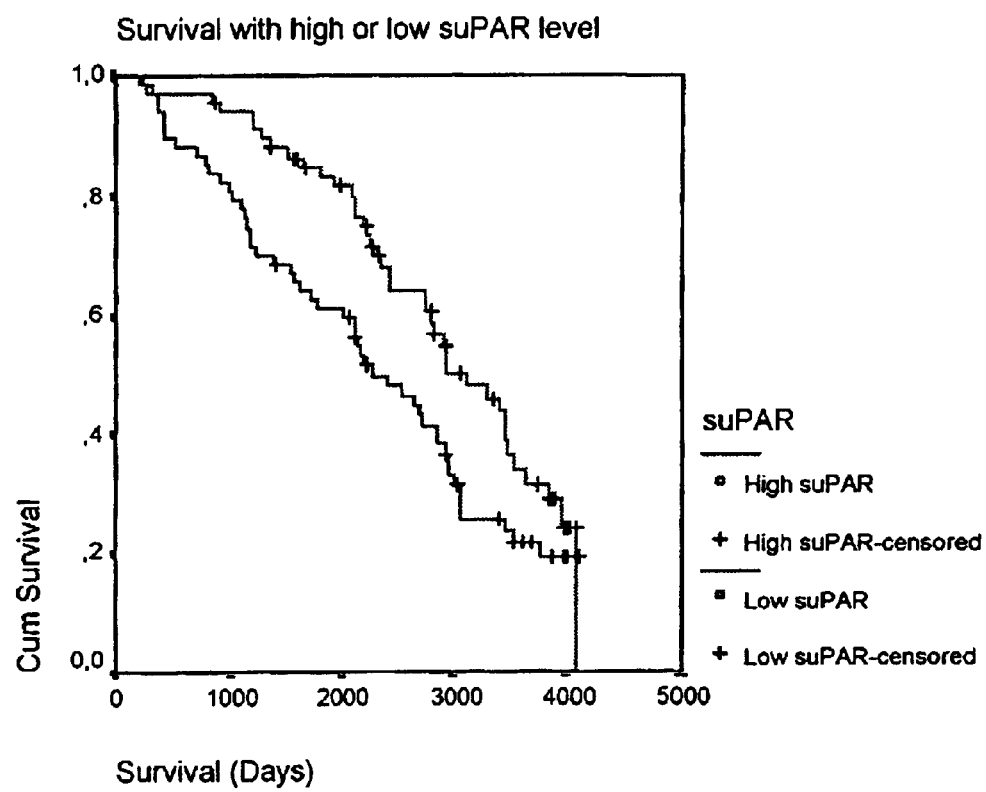
FIG. 6 is a plot of the survival period for high and low suPAR level patients.
Figure 7:
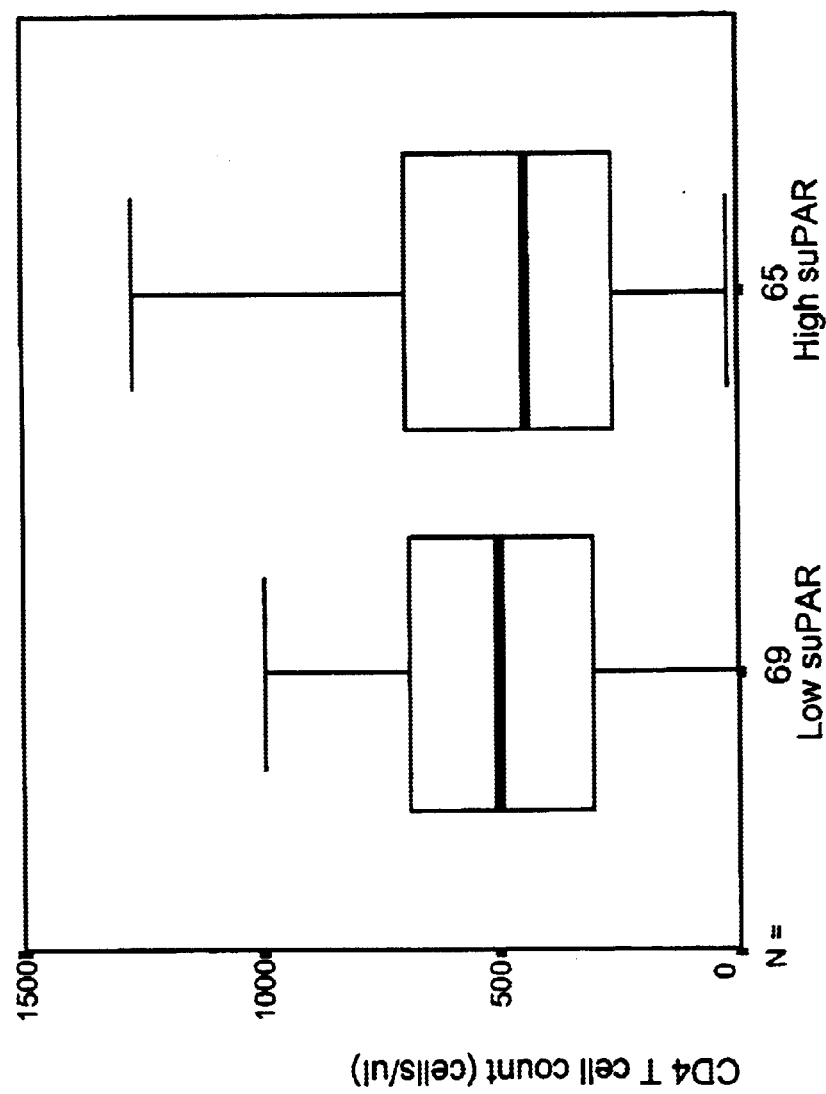
FIG. 7 is a chart showing the CD4 T cell counts for high and low suPAR level patients.

Results suPAR was measured retrospectively on serum from 133 patients using ELISA. All patients had measurable suPAR. The mean suPAR level was 1.87 ng/ml. When dividing the patients by median suPAR level (67/66), those with high suPAR progressed significantly faster towards AIDS as shown in the Kaplan Meier (FIG. 5). Mean time for progression to AIDS in the low suPAR group was 8.0 years, while those with high suPAR progressed to AIDS in 4.2 years. Similarly, in progression to death those with low suPAR died median 8.5 years after the suPAR measurement, and those with high suPAR level died median 6.6, years (FIG. 6) ($P<0.05$). Cox regression analysis (Table 2) showed that both suPAR and log transformed CD4 T cell counts was significantly associated with time to AIDS and death, and that the prognostic value of suPAR is independent of the CD4 T cell count. This is also demonstrated in FIG. 7, which shows no significant difference in CD4 T cell counts between those with low and those with high suPAR ($P=0.9$, t-test).

We observed no influence of PAI-1 4G/5G promoter polymorphisms on progression to AIDS or death ($P=0.6$).

Discussion

In this study, it was found that the serum level of soluble urokinase receptor is a strong prognostic factor in HIV infection. The reason for this is unknown, but may imply a specific role of the urokinase system in HIV infection/replication. It is possible that suPAR/uPA complexes may play an active role in HIV infection. The PAI-1 4G polymorphism has been reported to lead to increased levels of PAI-1 protein, compared to the PAI-1 5G genotype. In this study, no influence of PAI-1 promoter polymorphism on HIV disease progression was found.

In conclusion, previous findings showing that suPAR is a strong prognostic factor in HIV infection has been confirmed. Furthermore, the prognostic value of suPAR is independent of the CD4 T cell count.

TABLE 2

Cox regression uni and multi-variate analysis of time to AIDS or death

| | Patients | Univariate | Multivariate |
|---|---|---|---|
| suPAR | 133 | $P < 0.001$, RH = 1.42 Wald 19.5 | $P < 0.001$, RH = 1.40 Wald = 18.8 |
| CD4 (log10) | 133 | $P = 0.009$ RH = 1.64 Wald = 6.8 | $P = 0.011$, RH = 1.67 Wald = 6.5 |
| suPAR (aids) | 125 | $P = 0.011$, RH = 1.64 Wald = 6.4 | $P = 0.010$, RH = 1.64 Wald = 6.6 |
| CD4 (log10) (AIDS) | 125 | $P = 0.014$, RH = 1.72 Wald = 6.0 | $P = 0.013$, RH = 1.77 Wald = 6.2 |

Example 8

Strong Prognostic Value of suPAR in Both HIV-1 and HIV-2 Infected Individuals from Guinea Bissau Introduction Over the past decade, the HIV pandemic continues to evolve in most third world countries in both magnitude and diversity. Despite the reduction in numbers of new AIDS cases in the US and Western Europe due to advances in treatment, a constant number of new HIV infections persists every year. However, the vast majority of new infections still occur in developing countries, and Africa remains in focus of attention with the rapidly increasing epidemics in many countries in the south and east of the continent impacting on all levels of society.

There is no doubt that spread of public knowledge is an important factor in controlling the spread of the disease but development of inexpensive diagnostic/prognostic tools and anti-viral treatment are fundamental in the attempt to reduce severity and case-fatality rates in the developing countries.

In previous examples it has been reported that the soluble form of the urokinase receptor (suPAR) is a strong and independent prognostic factor in a cohort of Danish HIV-1 infected individuals. The serum level of suPAR is also a prognostic marker for overall survival in patients suffering from ovarian and colorectal cancer and for the response to therapy in leukaemia (10, 14). The urokinase receptor (uPAR) is an activation antigen in monocytes and T cells and T-cells from HIV-1 infected individuals express elevated levels of uPAR (3). HIV-1 infection of leukocytes in vitro causes up-regulation of uPAR cell surface expression in a process that appear to be coordinated temporally with the onset of viral replication (5). The receptor for urokinase-type plasminogen activator (uPAR/CD87) is anchored to the plasma membrane by a glycosyl phosphatidylinositol (GPI)-linkage. uPAR may be shed from the cell surface generating a soluble form of the receptor (suPAR) lacking the GPI-anchor. Soluble forms of uPAR (suPAR) has been identified in cell culture supernatants and in biological fluids such as cystic fluid, serum, plasma and urine (31).

suPAR is measured by a simple ELISA technique and may therefore be of aid in settings, such as Africa, were expensive equipment for measurement of CD4+ T cells and HIV viral load may not be available. Thus, in this example it is investigated whether HIV-1 and/or HIV-2 infected Africans from Guinea Bissau have elevated suPAR levels and whether the suPAR level carries prognostic value.

Subjects and Methods

Sera from 262 patients were available from the tuberculosis (TB) study. After informed consent to participate in the study, blood was drawn and sera tested for HIV antibodies. Five individuals (1 HIV-1 positive, 4 negatives) were tested at a clinical follow up examination only and not at the initial recruitment. HIV testing was performed at the National Public Health Laboratory. Sera were screened using Enzygnost® Anti-HIV 1+2 Plus (Behring Diagnostics Gmbh, Marburg, Germany) and confirmed with Capillus® HIV-1/HIV-2 (Cambridge Diagnostics, Galway, Ireland) or Multispot® HIV-1/HIV-2 (Sanofi Diagnostics Pasteur, Marnes-la Coquette, France). Dual reactive samples were sent frozen to Swedish Institute for Infectious Diseases (SMI) in Stockholm and confirmed using Immunocomb® II Hiv-1&2 Bispot (Orgenics, Yavne, Israel). The study protocol was approved by the Central Ethical Committee of Denmark and by the Ministry of Health of Guinea-Bissau. Transmission route for HIV infection is not known, although the majority are sexual transmissions. Homosexuality is not common in Guinea Bissau.

The CD4- and CD8-cells was counted using the Immuno-Alkaline phosphatase method (IA) (32).

suPAR was measured retrospectively on thawed serum samples by a sensitive ELISA system (9). The following minor modifications of the technique were used: Bovine serum albumin (2% in phosphate buffered saline) was used as a blocking reagent instead of SuperBlock™, and reactions were stopped with 100 ul 1 M NaOH after 30 minutes instead of kinetic substrate development. These modifications did not affect the sensitivity or specificity of the assay.

Statistics

All statistical analyses were performed using the statistical program SSPS, Version 10. Comparisons of proportions were performed using the Chi-square test. Comparison of unpaired observations was carried out using Kruskal-Wallis test. Kaplan-Meier curves were constructed by stratifying the patients by the median suPAR level in all HIV positive patients. The difference between Kaplan-Meier curves was analysed by the log-rank test and the differences between groups by Cox regression. The ability of serum suPAR to predict mortality in the context of other known prognostic markers was formally assessed using the Cox proportional hazards model. Variables were fitted in a continuous scale using the strongest transformation (as determined by the Wald $\chi^2$ value) of the individual variables (log-scale CD4 count and linear scale for suPAR and TB diagnosis as yes/no). A significance level of 5% was used.

Results

Sera from 262 patients were analysed. All patients had measurable suPAR (range 0.9–18.7, mean 3.3 ng/ml). Of the 262 patients, 113 were HIV positive (28 with HIV-1, 66 with HIV-2 and 19 were dual-infected) and 149 were HIV negative. Regarding pulmonary disease, 198 patients were found to be TB positive (sputum confirmed or clinically suspected) and 64 patients were regarded as having non-TB disease (pneumonia or bronchitis).

SuPAR is Prognostic for Survival in HIV Positive African Individuals

Figure 8:
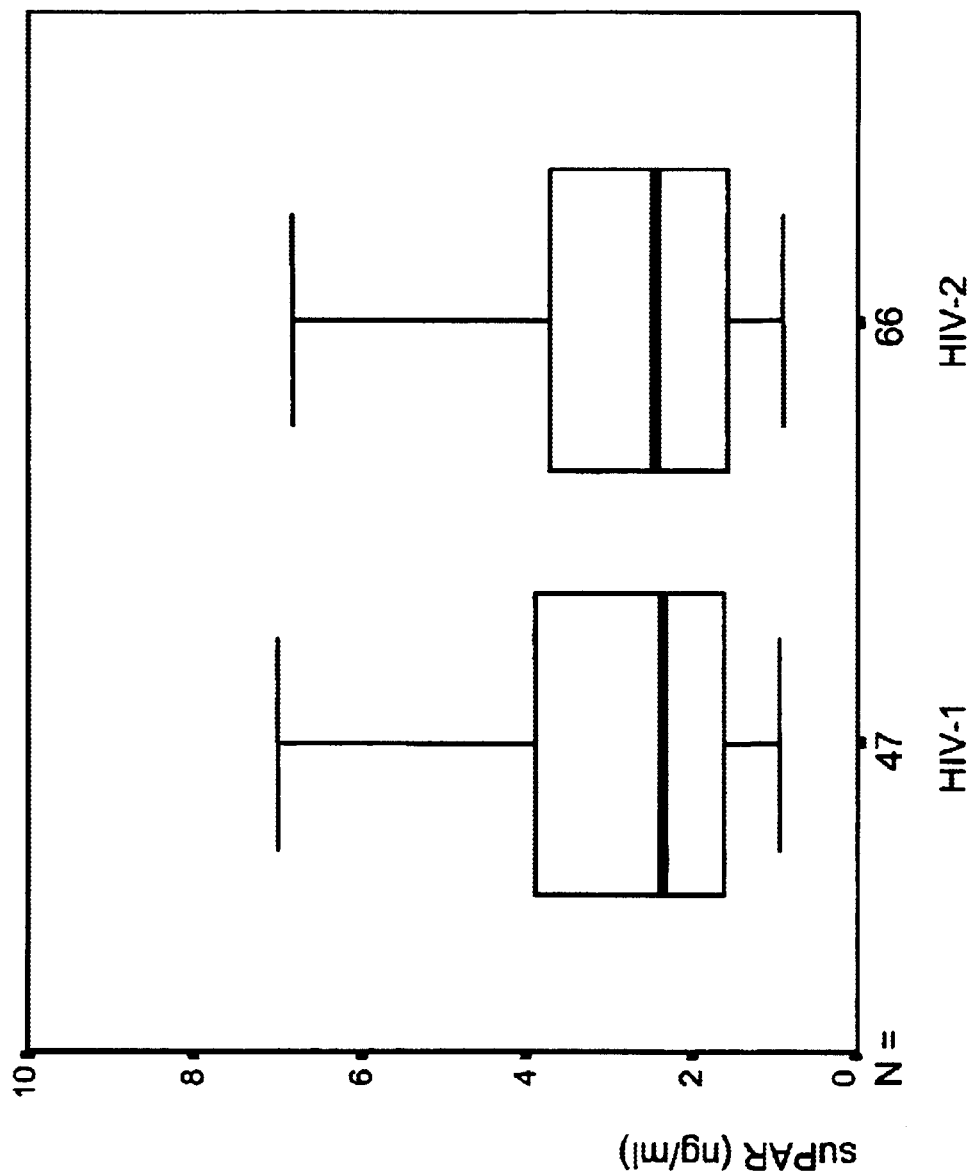
FIG. 8 is a chart showing the suPAR level for HIV-1 and HIV-2 patients.

There was a trend for higher suPAR levels among HIV positive compared to HIV negative (P=0.061, Kruskal Wallis test). There was no difference in suPAR level between those HIV-1, HIV-2 or dual infected (FIG. 8). Individuals HIV+/TB+ (N=87) had higher suPAR levels than those HIV+/TB negative (N=26) (P=0.049)(Table 3).

Figure 9:
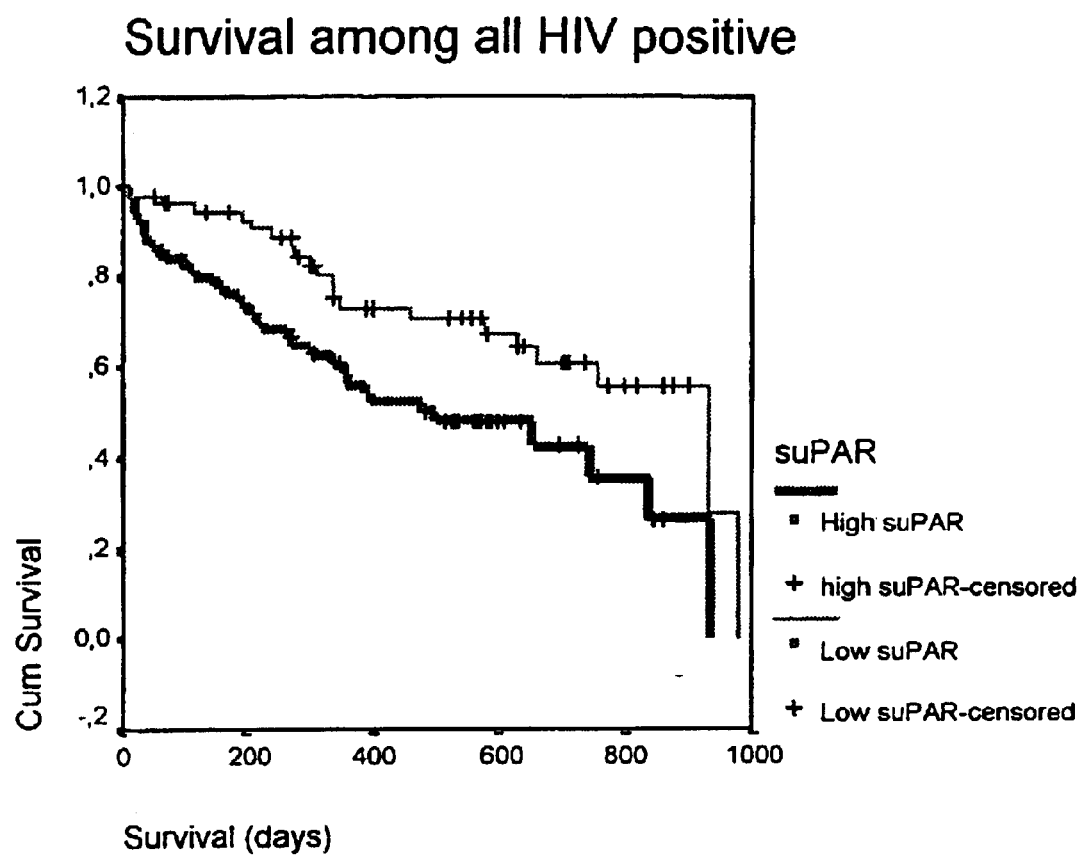
FIG. 9 is a plot of the survival period for all HIV positive patients.

Kaplan Meier: The HIV positive individuals were split into two groups based on the meridian suPAR level. In the low suPAR group (N=57) median time of survival was 933 days (95% CI: 684–1182 days). In the high suPAR group (N=56), median survival was 495 days (95% CI: 202–788 days). The difference in survival between the two groups was significant (p=0.012, log rank) (FIG. 9). When dividing the HIV positive patients according to whether they were infected with HIV-1 (the HIV-1 group also included the dual infected) or HIV-2, suPAR was prognostic for the outcome of both the HIV-1 infected (FIG. 10) and HIV-2 infected (FIG. 11).

Cox regression: The following parameters were found to be significantly associated with survival in a univariate Cox regression analysis: Log10 transformed CD4 counts (p=0.030, N=90), TB diagnosis (0.004, wald 8.1, RH=1/ 0.388 N=113) and suPAR (p<0.001, wald 19.3, RH=1.2, N=113) (table 1). Age and CD8 T cell counts were not significantly associated with survival (p=0.7 and 0.5 respectively). In a multivariate Cox regression model, all data were available in 90 patients, suPAR (p<0.001, wald 19.1, RH per ng increase in suPAR 1.2) and TB diagnosis. (p=0.005, wald 8.0, RH for TB+=3.12), but not logCD4 count (p=0.35, wald=0.8) were associated with survival.

SuPAR is elevated in TB positive patients, but carry no prognostic value.

Figure 12:
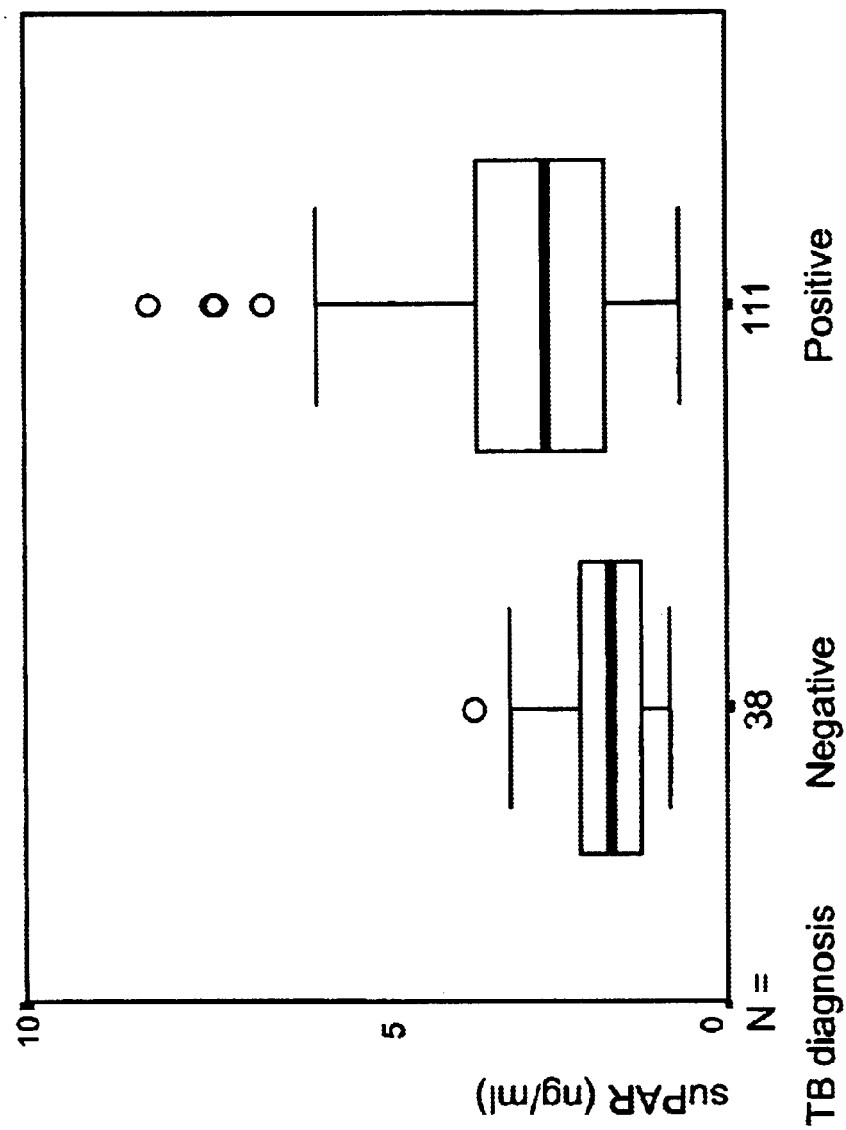
FIG. 12 is a chart showing the suPAR level for tuberculosis negative and positive patients.

Among the 149 HIV negative individuals, 111 were found to be TB positive. Those who were TB positive had significantly higher suPAR levels compared to the 38 individuals who were clinically diagnosed as TB negative (p=0.001, Kruskal Wallis test), FIG. 12. During follow up, twenty of the TB positive died. suPAR level was not significantly associated with survival for TB+individuals (n=111, p=0.23, Table 3).

TABLE 3 shows the suPAR levels among HIV infected according to type of infection as well as HIV negative according to TB status. In the cox regression analysis, suPAR was entered untransformed, while CD4 counts were log10-transformed.

|  | N | suPAR mean (range) | Cox | RH | N | CD4 (mean, range) | Cox | RH |
|---|---|---|---|---|---|---|---|---|
| HIV positive | 113 | 3.3 (0.91–18.70) | P < 0.001 | 1.18 | 90 | 510 (132–1278) | P = 0.03 | 3.13 |
| HIV1 or dual | 47 | 3.4 (0.94–18.7) | P < 0.001 | 1.37 | 38 | 456 (132–1083) | P = 0.11 | 5.35 |
| HIV-1 TB pos | 42 | 3.5 (0.92–18.70) | P = 0.001 | 1.39 | 34 | 472 (161–1083) | P = 0.23 | 3.52 |
| HIV-2 | 66 | 3.2 (0.91–18.3) | P = 0.002 | 1.17 | 54 | 549 (142–1278) | P = 0.25 | 2.99 |
| HIV-2 TB pos | 50 | 3.5 (0.91–18.33) | P < 0.001 | 1.23 | 42 | 661 (142–1156) | P = 0.56 | 1.91 |
| HIV neg TB neg | 38 | 2.2 (0.80–16.2) | P = 0.82 | 1.26 | 37 | 1235 (382–3789) | P = 0.20 | 1.0 |
| HIV neg TB pos | 111 | 3.0 (0.66–13.3) | P = 0.23 | 1.12 | 95 | 1078 (0–2832) | P = 0.64 | 0.65 |

Discussion

The serum suPAR level in 262 individuals enrolled in a cohort on suspicion of TB has been measured. Among these, 113 individuals were found to be HIV positive. SuPAR was strongly correlated with survival among these HIV positive individuals. We observed no difference in suPAR levels between HIV-1, HIV-2 or dual infected individuals indicating that suPAR carry general prognostic value in HIV infection. Other prognostic factors were CD4 T cell count (log transformed) and TB status. In a multivariate Cox analysis, only suPAR and TB status was associated with survival. In our previous study, the CD4 count was significantly associated with survival in a multivariate model (26). This difference may be due to different CD4 T cell counting methods in the two studies i.e. FACS versus the Immuno-Alkaline phosphatase method (33).

Among the 149 HIV negative individuals studied, 111 were found to be TB positive. Significant higher suPAR levels among the TB positive/HIV negative patients compared to the TB negative/HIV negative patients were observed. However, no prognostic value of suPAR among the TB positive/HIV negative, where twenty died during follow-up, was found.

The strong prognostic role of suPAR in HIV infected individuals may imply a direct role of the plasminogen activator system in HIV infection. In contrast, no prognostic role of suPAR was found among the TB positive/HIV negative compared to the TB negative/HIV negative, and the elevated suPAR level among the TB positive may reflect a general immune activation.

It is necessary to find cheap and efficient ways to monitor and treat HIV disease in Africa. Measurement of suPAR is technically simple (ELISA followed by OD measurement at 405 nm).

Example 9

The Serum Level of Soluble Urokinase-Type Plasminogen Activator Receptor is a Strong and Independent Predictor of Survival in HIV Infection HIV-1 infection has been shown to result in up-regulation of the urokinase-type plasminogen activator receptor (uPAR/CD87) on leukocytes in vitro and in vivo. The objective of this study was to investigate whether this upregulation is paralleled by higher serum levels of soluble uPAR (suPAR) in patients with advanced HIV-1 disease, and whether the serum level of suPAR is predictive of clinical outcome. Using an enzyme linked immunosorbent assay (ELISA) we measured the level of suPAR retrospectively in serum samples from 314 HIV-1 positive individuals. By Kaplan-Meier and Cox regression analyses the serum suPAR levels were correlated to survival with AIDS related death as endpoint. High levels of serum suPAR (>median) were associated with poor overall survival and Kaplan-Meier analysis on patients stratified by suPAR level demonstrates a continuous increase in mortality with higher suPAR levels. After adjustment for accepted prognostic markers including the Centers for Disease Control (CDC) defined clinical stages, CD4 counts, viral load, $\beta$2-microglobulin, and age, the prognostic strength of suPAR remained highly significant indicating that the serum suPAR level is a novel, strong and independent predictor of survival in HIV-1 infection. This report is the first to demonstrate an important association between the plasminogen activator system and disease progression in HIV-1 infection.

Introduction

The urokinase-type plasminogen activator system consists of a proteinase (uPA), a receptor (uPAR) and inhibitors. The system is involved in pericellular proteolysis, cell migration, and tissue remodeling by multiple modes of action i.e. proteolysis, signal transduction, and chemokine-like activities (1,34). Under physiological conditions uPA and uPAR is predominantly expressed by blood cells including neutrophils, monocytes, macrophages and activated T-cells (35) for which they are believed to play important roles in cell activation, adhesion, migration and extravasation (36,37,38).

High serum levels of suPAR, the soluble form of uPAR, have recently been associated with worse overall survival of cancer patients (10,12) and it has been suggested that in cancer the excess of suPAR in the circulation derives from tumor tells or tumor infiltrating macrophages (10, 12, 7, 17) which often express high levels of uPAR (39).

The fact that enhanced serum suPAR levels are indicative for up-regulated cellular uPAR levels, combined with the previously published data that HIV-1 infection leads to enhanced cell surface expression of uPAR on mononcytes and T-lymphocytes both in vitro and in vivo (3, 4, 5) prompted us to investigate the relationship between serum suPAR levels in HIV-1 infected individuals and progression of the disease.

Methods

Patients

The Copenhagen HIV Immune Cohort (CHIC) is a seroprevalent cohort consisting of 347 HIV-1 infected patients enrolled from the Department of Infectious Diseases at Rigshospitalet, Copenhagen, Denmark, between September 1991 and October 1992 as previously described (25). The cohort was followed from inclusion until June 1997, however in the current study follow-up was censored when the first patient in the cohort received a protease inhibitor (1$^{st}$ May 1996). Thirty-three patients (9.5%) for whom a serum sample was not available were excluded from this study.

There were no significant differences in follow-up time, age, CD4 count, viral load, and β2-microglobulin level between patients in the current study and those excluded. At enrolment into CHIC, blood was drawn for determination of CD4 count, and other serological parameters related to HIV-1 progression. Of the 314 serum samples available for suPAR measurement, 208 were obtained at the time of enrolment (baseline) and the remaining 106 close to the time of enrolment (median: 0.9 month before, range: 8.4 month before to 7.2 month after). All other serological values used in this study were baseline values. Clinical staging of the patients was performed according to the 1993 Centers for Disease Control (CDC) AIDS surveillance case definition for adolescents and adults. Of the 314 patients included in this study 230 (73.2%) received anti-retroviral treatment with one or more nucleoside reverse transcriptase inhibitors (NRTIs) before enrolment or during follow-up. Of these patients 140 (60.9%) received one, 88 (38.3%) two and 2 (0.9%) three NRTIs. No patients ever received three NRTIs simultaneously. Follow-up times were calculated from the date of enrolment and up to the date of death (caused by AIDS) or censored at the $1^{st}$ of May 1996. The data were cross-checked with the Danish National Registry System and patients who were lost during follow-up were censored at the last day they were known to be alive.

Measurement of serum suPAR, CD4 count, viral load and β2-microglobulin.

suPAR was measured retrospectively on thawed serum samples by a sensitive ELISA system (12, 17). Samples were measured in duplicates and inter-plate variation was, if necessary, corrected by the inclusion of a reference sample on all plates. With respect to the published method the following minor modifications of the technique were used: Bovine serum albumin (2% in phosphate buffered saline) was used as a blocking reagent and endpoint measurements were used instead of kinetic substrate development. CD4 count, viral load and β2-microglobulin level had previously been determined in the majority of these patients (20, 18).

Statistical Analysis

All statistical analyses were performed using statistical packages (SSPS, Version 8 and SAS® version 6.12) and the observed differences were considered significant if the p-value was below 0.05. Comparisons of proportions were performed using the Chi-square test. Comparison of unpaired observations for continues variables was carried out using Kruskal-Wallis or Mann-Whitney U-tests. Correlation's were calculated using the Spearman rank test. Kaplan-Meier curves were constructed stratifying the patients by the level of serum suPAR to generate similar number of patients in each stratum. Differences between Kaplan-Meier curves were analyzed by the log-rank test and by Cox regression. The ability of serum suPAR to predict mortality in the context of other known prognostic markers was formally assessed using a multivariate Cox proportional hazards model. Variables were fitted in a continuous scale using the transformations which provided the best fit as determined by the Wald $\chi^2$ value (log-scale for viral load, CD4 count and β2-microglobulin, and linear scale for suPAR and age).

Results

Levels of suPAR in Serum

All 314 HIV-1 infected patients had measurable levels of serum suPAR with a median value of 3.69 ng/ml (range: 1.15–15.60 ng/ml). Division of all patients into two equal groups by the median suPAR level revealed several significant differences (Table 3). Patients with high suPAR had a shorter follow-up time (p<0.0001) caused by an increased incidence of AIDS-related death (p<0.0001), lower CD4 count (p<0.0001), higher viral load (p=0.002), higher β2-microglobulin level (p<0.0001) and were older (p=0.007). No significant differences were observed with respect to the gender of the patients (p=0.7), the route of infection (p=0.2), or whether the patients received anti-retroviral treatment at the time of enrolment (p=0.3).

Division of the patients into three groups by the CDC defined clinical stages A, B and C (FIG. 13) demonstrated that more advanced HIV-1 disease was associated with higher levels of serum suPAR (p<0.0001, Kruskal-Wallis test).

Figure 13:
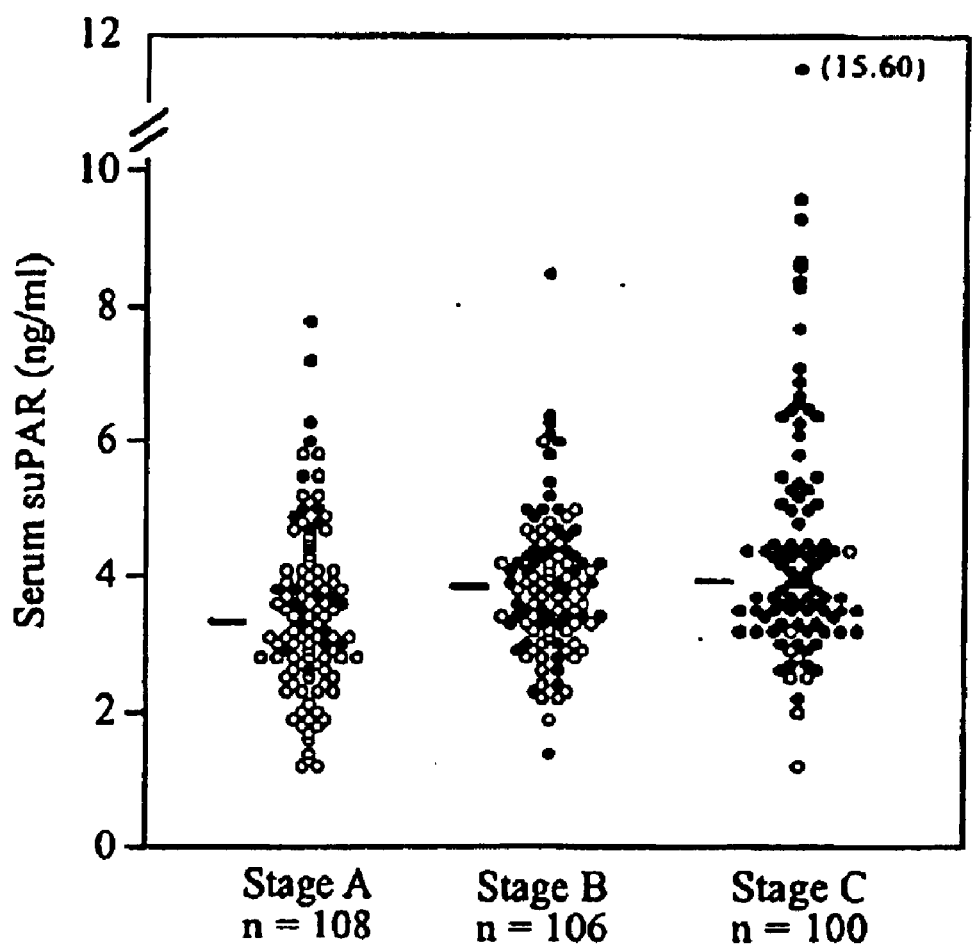
FIG. 13 is a chart of serum suPAR levels in patients with HIV-1 disease stages A, B and C.
Figure 14:
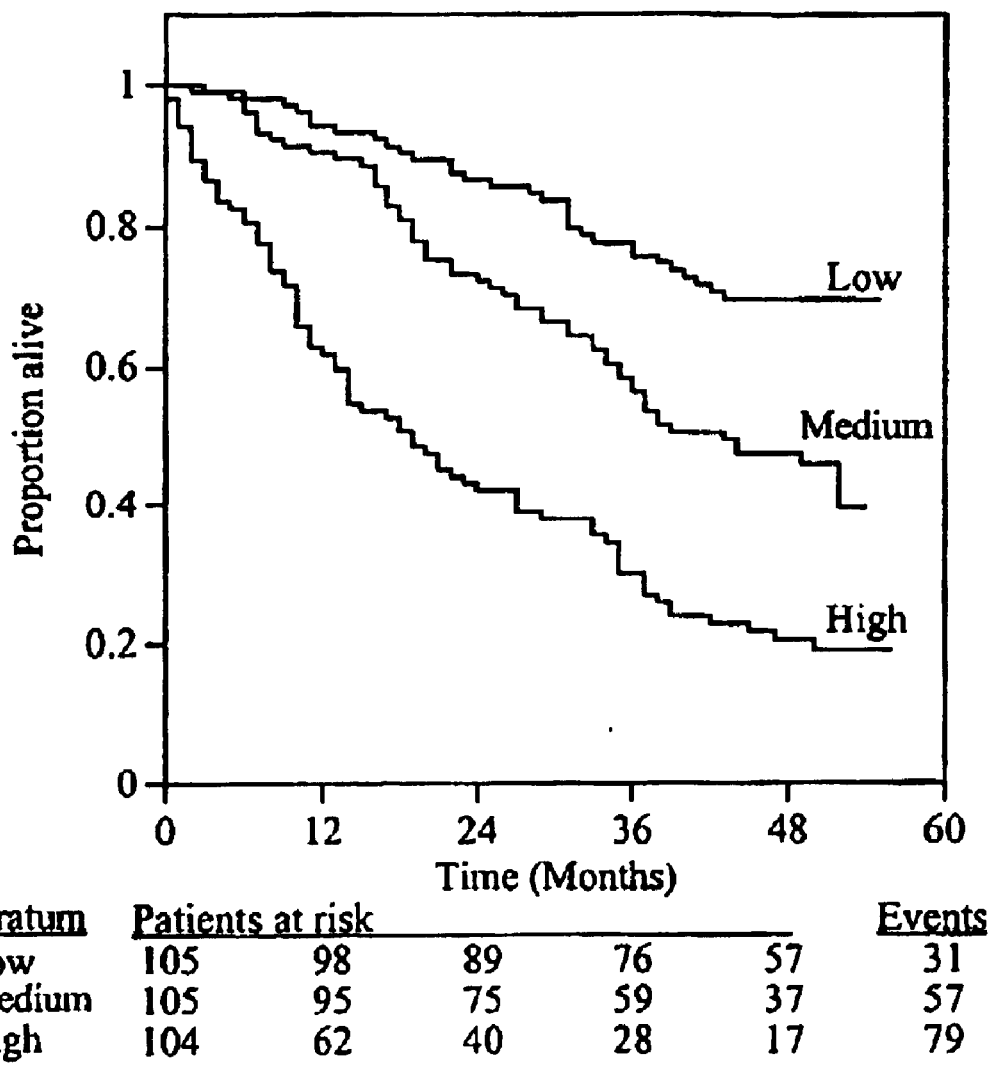
FIG. 14 is a plot of the survival rate vs. time for low, medium and high suPAR level patients.

FIG. 13 shows serum suPAR levels in patients with CDC defined HIV-1 disease stages A, B and C. Each patient is indicated by a circle and a filled circle indicates that the patient died during follow-up. Median values of suPAR within each stage are indicated by horizontal bars. The serum suPAR levels between the clinical stages were significantly different (P<0.0001, Kruskal-Wallis test). Proportions of patients who survived was significantly higher in patients with low levels of suPAR (below the median in the respective group) in all three CDC stages (Chi-square test): Stage A: p=0.006; stage B: p=0.03; stage C: p=0.03.

Within each of the clinical stages A, B and C the proportion of survivors was significantly (p=0.03, Chi-square test) higher among patients with suPAR levels below the median, indicating a possible correlation between suPAR levels and survival at different stages of HIV-1 infection.

Spearman rank correlation's demonstrated a weak but significant negative correlation between suPAR and CD4 count (Rho=−0.33, p<0.0001), and weak but significant positive correlation's between suPAR and viral load (Rho=0.28, p<0.0001), between suPAR and β2-microglobulin (Rho=0.45, p<0.0001), and between suPAR and age (Rho=0.18, p=0.002).

Kaplan-Meier Analysis

To investigate the association between suPAR levels and survival a Kaplan-Meier analysis (FIG. 11) has been performed.

Association between the level of suPAR in serum from 314 HIV-1 infected patients and overall survival. Patients were divided into three strata based on the serum suPAR values, yielding similar number (n=104–105) of patients in each stratum. The three curves in the figure thus represent patients with serum suPAR<3.28 ng/ml (Low), 3.28–4.19 ng/ml (Medium), and >4.19 ng/ml (High). The overall difference between the groups was highly significant (p<0.0001, $\chi^2$=63, log-rank test). The number of patients at risk after each 12-month interval is indicated below the figure.

In the absence of any relevant cut-off value for serum suPAR use was made of the 33% and 66% percentile of suPAR levels, generating three groups of patients of similar size (n=104–105 patients) representing low, medium and high serum suPAR levels. The survival curve for patients with low serum suPAR were significantly different from that of medium suPAR (p=0.0008, $\chi^2$=11, log-rank test) which in turn was significantly different from that of patients with high suPAR (p<0.0001, $\chi^2$=26, log-rank test).

Cox Regression Analysis

Figure 10:
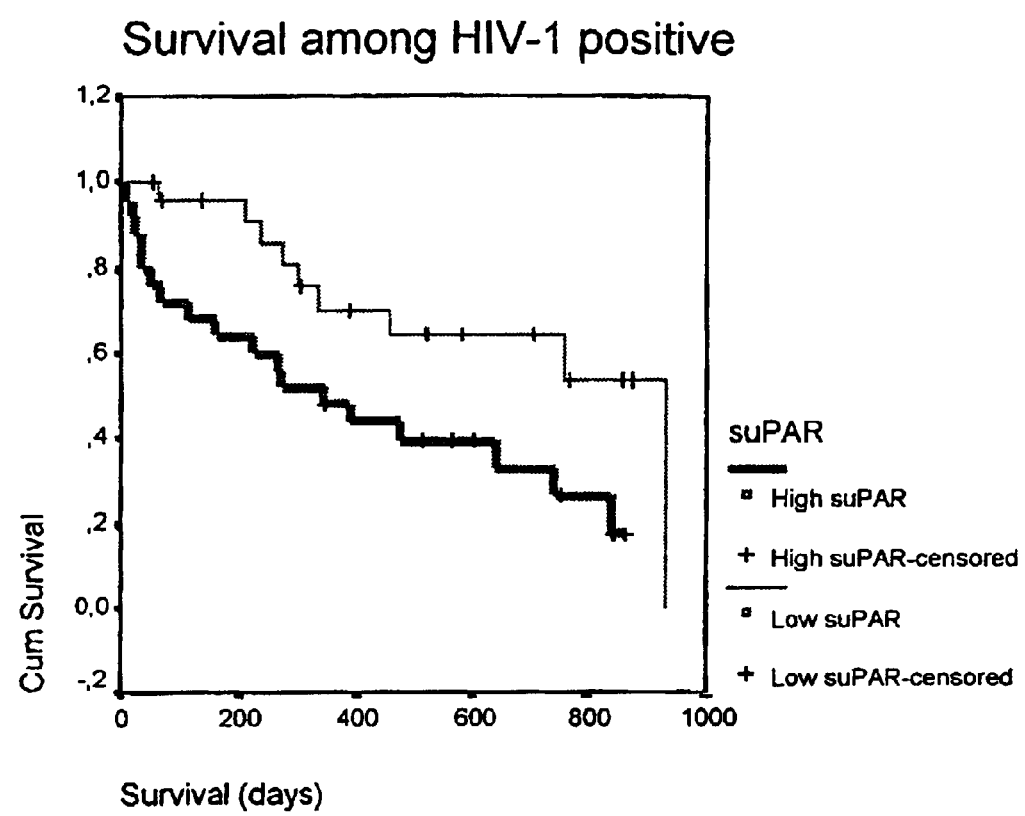
FIG. 10 is a plot of the survival period for HIV-1 positive patients.
Figure 11:
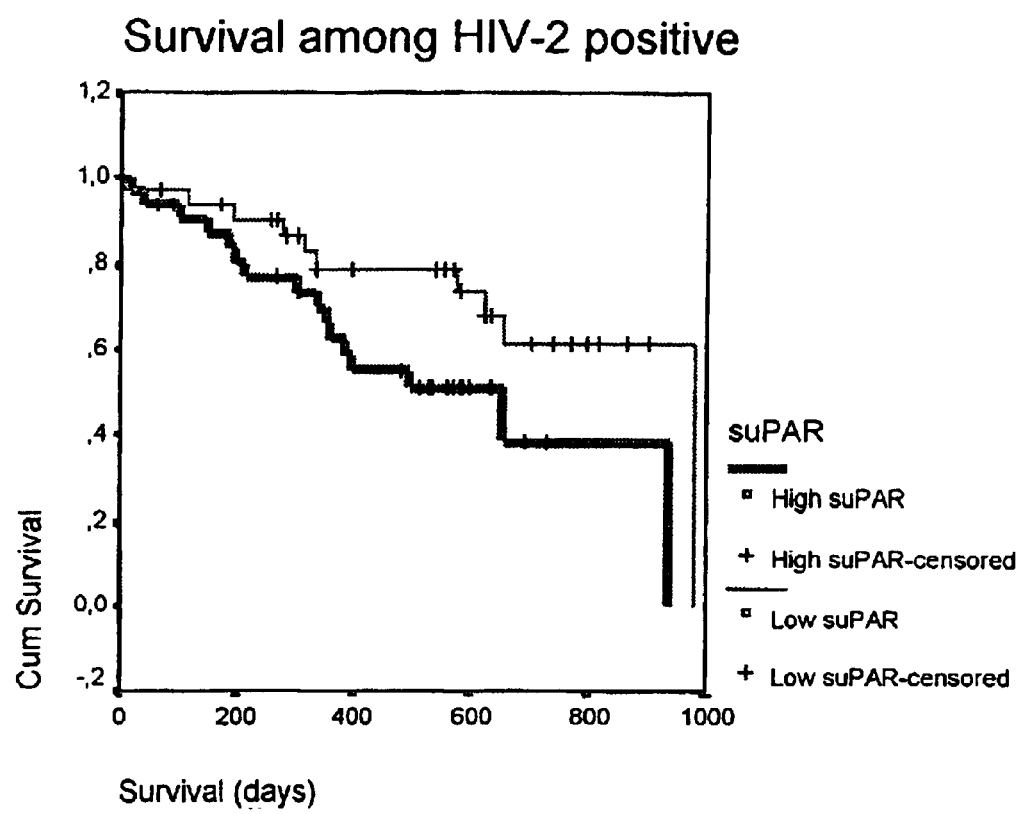
FIG. 11 is a plot of the survival period for HIV-2 positive patients.

Comparison of the three patient groups in the Kaplan-Meier plot (FIG. 10 by Cox regression analysis demonstrated a continuously increasing risk of morality with increasing suPAR level. Compared to patients with a low suPAR level, a medium suPAR level was associated with a hazard ratio (HR) of 2.2 (95% confidence interval (95% CI): 1.4–3.4, p<0.0001) and a high suPAR level with a HR of 4.7

(95% CI: 3.1–7.2, p<0.0001). Compared to patients with a medium suPAR level, a high suPAR level was associated with a HR of 2.2 (95% CI: 1.6–3.1, p<0.0001).

When suPAR was fitted as a continues variable in a Cox model including all patients high levels of suPAR were significantly associated with an increased mortality (Table 5). An increase in serum suPAR of 1 ng/ml was associated with a HR of 1.6 (95% CI: 1.5–1.8, p<0.0001). Other clinical and serological variables which provided significant prognostic value in univariate Cox analysis were CD4 count, viral load, β2-microglobulin level, age, clinical stage and drug treatment at enrolment. As expected, the well established and clinically used prognostic marker CD4 count provided the best fit in univariate analysis as estimated by the Wald $\chi^2$ value.

Patients for whom data for all the serological variables were available (n=231) were then fitted with suPAR in a multivariate Cox regression model (Table 11). The predictive strength of suPAR in this subset (n=231) of patients was virtually identical to when the analysis was performed on all 314 patients (not shown). In the multivariate Cox model suPAR, CD4 count, viral load, β2-microglobulin and CDC stage C, provided statistically significant independent prognostic information. According to the Wald $\chi^2$ value, suPAR was a stronger predictor of survival than the CD4 count and viral load.

TABLE 4

Patients characteristics

| Clinical data | All n = 314 | Low suPAR = 3.69 ng/ml n = 157 | High suPAR > 3.69 ng/ml n = 157 | Low vs. High p-value |
|---|---|---|---|---|
| Median follow-up time (months) (Range) | 38 (0.3–57) | 48 (2.5–55) | 23 (0.3–57) | <0.0001** |
| AIDS caused death | 167 | 64 | 103 | <0.0001†† |
| Drug at enrolment* | 161 | 76 | 85 | 0.3†† |
| Gender (males/females) | 280/34 | 141/16 | 139/18 | 0.7†† |
| Median Age (years) (Range) | 39 (16–66) | 37 (20–60) | 41 (16–66) | 0.007** |
| Route of infection | | | | |
| Homosexual contact | 241 | 123 | 118 | 0.7†† |
| Heterosexual contact | 46 | 24 | 22 | 0.5†† |
| Other† | 27 | 10 | 17 | 0.2†† |
| Serological variables | | | | |
| Median CD4 count (cells/mm$^3$) (Range) | 204 (0–1116) n = 305§ | 264 (1–992) n = 154 | 130 (0–1116) n = 151 | <0.0001** |
| Median viral load‡ (Range) | 5.02 (2.30–6.86) n = 250§ | 4.78 (2.30–6.72) n = 125 | 5.20 (2.30–6.86) n = 125 | 0.002** |
| Median β2-microglobulin (nM) (Range) | 218 (0–1802) n = 295§ | 200 (0–530) n = 150 | 248 (0–1802) n = 145 | <0.0001** |
| Median suPAR (ng/ml) (Range) | 3.69 (1.15–15.60) | 3.03 (1.15–3.69) | 4.46 (3.70–15.60) | NA |

*Patients in anti-retroviral drug treatment at the time of enrolment.
†Six patients were infected by intravenous drug use, seven by contaminated blood transfusions, six were haemophilia patients, and eight had unknown route of infection.
‡log$_{10}$ HIV-1 RNA molecules/ml plasma.
§Nine patients with missing data for CD4 count, sixty-four patients with missing data for viral load, and nine-teen patients with missing data for β2-microglobulin.
**Mann-Whitney U-test.
††Chi-square test.
NA, not applicable.

* Patients in anti-retroviral drug treatment at the time of enrolment.
† Six patients were infected by intravenous drug use, seven by contaminated blood transfusions, six were haemophilia patients, and eight had unknown route of infection.
‡ log$_{10}$ HIV-1 RNA molecules/ml plasma.
§ Nine patients with missing data for CD4 count, sixty-four patients with missing data for viral load, and nineteen patients with missing data for β2-microglobulin.
** Mann-Whitney U-test.
†† Chi-square test.
NA, not applicable.

TABLE 5

Cox regression analysis

| | Univariate | | | Multivariate (n = 231†) | | |
|---|---|---|---|---|---|---|
| Variable | p-value | Hazard Ratio (95% CI*) | Wald $\chi^2$ | p-value | Hazard Ratio (95% CI*) | Wald $\chi^2$ |
| suPAR 1 ng/ml higher | <0.0001 | 1.6 (1.5–1.8) | 107 | <0.0001 | 1.5 (1.3–1.7) | 33 |
| CD4 count 50% lower | <0.0001 | 1.6 (1.5–1.7) | 200 | <0.0001 | 1.3 (1.1–1.5) | 15 |
| Viral load 10-fold higher | <0.0001 | 3.9 (3.0–5.2) | 94 | <0.0001 | 2.0 (1.4–2.7) | 17 |
| β2-microglobulin 2-fold higher | <0.0001 | 3.0 (2.3–3.8) | 71 | 0.02 | 1.3 (1.0–1.6) | 5 |
| Age 10 years older | 0.03 | 1.2 (1.0–1.4) | 5 | 0.06 | 1.2 (1.0–1.5) | 4 |
| CDC Stage B vs. A | <0.0001 | 2.7 (1.7–4.4) | 16 | 0.4 | 1.3 (0.7–2.3) | 1 |
| CDC stage C vs. A | <0.0001 | 12.3 (7.8–20.0) | 113 | 0.005 | 2.8 (1.4–5.7) | 8 |
| Drug treatment at enrolment (yes vs. no) | <0.0001 | 2.6 (1.9–3.7) | 35 | 0.1 | 1.5 (0.9–2.3) | 3 |

*95% confidence interval of the hazard ratio.
†Patients for whom data for one or more of the serological variables was missing (n = 83) were excluded from the analysis (see table 1 for details).

Discussion

In the present work evidence has been provided that serum suPAR is a strong independent prognostic variable in HIV-1 infection. In Kaplan-Meier survival analysis higher serum levels of suPAR are associated with faster progression to death. After adjustment for all known relevant HIV-1 disease progression markers in multivariate Cox regression analysis suPAR remains a highly significant independent predictor of survival. This is to our knowledge the first report demonstrating a connection between the urokinase plasminogen activator system and disease progression in HIV-1 infection.

One possible explanation for the prognostic value of serum suPAR in HIV-1 infection is that it derives, at least partially, from HIV-1 infected cells. Monocytes and T-lymphocytes infected with HIV-1 have been shown to express elevated levels of cell-surface uPAR (3, 4, 5) and the serum level of suPAR may correlate with the size of the reservoir of HIV-1 infected cells in the organism. This model predicts that suPAR levels will be higher in HIV-1 infected individuals than in healthy controls, a possibility which we have not addressed in this study.

However, in accordance with this hypothesis, our data do demonstrate that the suPAR level is higher in patients with more advanced HIV-1 infection.

The striking correlation between suPAR levels and the risk of disease progression may suggest a direct relevance of uPAR in HIV-1 infection. The natural high-affinity ligand of uPAR, uPA, has been shown to bind HIV-1 gp120 and promote HIV-1 infection of macrophages in vitro (27). The interaction between uPA and gp120 involves the functionally important V3-loop of gp120 and the catalytic domain of uPA, but leaves the ligand binding domain of uPA free for interaction with uPAR (27). It is thus possible that uPA may form a "bridge" between gp120 on the virus and uPAR on the cell surface which would identify uPAR as a cellular co-receptor for HIV-1. Indeed, it should be noted that the major cell types susceptible to HIV-1 infection are those in which uPAR is predominantly expressed (macrophages, activated monocytes and T-cells). Investigations addressing such an involvement now seem highly warranted.

Finally, it should be emphasized that circulating suPAR might play a direct role in the pathogenesis of HIV-1 infection. In fact, suPAR fragments have chemokine-like activities and suPAR is capable of modulating processes such as cell adhesion, migration, and proliferation in vitro (1, 34).

Regardless of the biological explanation, the serum level of suPAR remains a strong and independent prognostic predictor of disease progression in HIV-1 infection. Using a single serum suPAR measurement and arbitrary cut-off points we were able to define patient groups associated with different hazard ratios for disease progression, suggesting that suPAR measurements may be used as a prognostic tool in HIV-1 infection.

The variables suPAR, CD4 count and viral load were only poorly correlated mutually and all three parameters provided highly significant independent prognostic information in multivariate Cox analysis. This implies that suPAR provides important additional prognostic information. In this respect it will be particularly important to determine if suPAR is useful in determining if and when to initiate highly active anti-retroviral therapy (HAART).

There is still considerable debate, as reflected in different national guidelines, about what combination of CD4 count and viral load constitutes an indication for therapy. Virologic and immunologic arguments for early initiation of therapy need to be balanced against disadvantages of treatment such as lifelong polypharmacy, high costs, side effects, and risk of resistance development. As the suPAR level carries strong and independent information on the progression status, it may aid in the monitoring of patients and in the important clinical decision of when to initiate HAART.

In the current study follow-up was censored at the date when the first patient in the cohort received a protease inhibitor, and the patients therefore only received relative light anti-retroviral treatment as compared to HAART. The treatment with anti-retroviral drugs at the time of enrolment in CHIC was associated with poor survival in univariate Cox analysis, but failed to provide significant prognostic information in multivariate Cox analysis. This most likely reflects the fact that patients who had received treatment at the time of enrolment were those with a more advanced disease for whom mono- or dual-therapy did not provide a strong survival benefit. The present study is therefore likely to reflect disease development close to the natural history course of HIV-1 infection and the possible prognostic value of suPAR in the context of HAART should be addressed in other more appropriately designed studies.

Although the present study shows a strong association between suPAR levels and disease progression it is important to realize that the amount of data from this single study does not justify suggestions of using suPAR as a standard prognostic parameters. First the data needs to be confirmed in an independent cohort. Secondly since this cohort consists of patients in a European country before the HAART era its value needs to be confirmed in patients with access to HAART treatment and/or in resource poor settings. This study makes use of arbitrarily chosen cut-off values and statistical methods, which do not require the definition of specific cut-off values. Normal values of suPAR obtained using standardized sample techniques needs to be determined before routine use of suPAR can be applied.

It has recently been shown that suPAR antigen can be readily quantified in urine, and that the urinary suPAR level strongly correlates with the serum level (14). It is therefore possible that urine may provide an alternative to serum samples for suPAR based HIV-1 prognosis, which would introduce an element of safety and convenience for both the patients and the medical staff.

The introduction of HAART in the western world has profoundly increased the life expectancy of HIV-1 infected individuals. However, because of the high cost of these drugs only a small fraction of the HIV-1 infected persons in the world have access to effective HIV-1 therapy. The measurement of suPAR is performed using a simple and inexpensive ELISA technique. After confirmation of our results in other groups of patients, the determination of suPAR in serum (or even better urine) from HIV-1 infected persons may provide a cost-effective supplement or alternative to the currently used "decision making" tools based on CD4 counts and viral load.

Example 10 suPAR ELISA (R2/Pab)

In the following, an example of a specific ELISA suitable for use in the method of the invention is given.

Figure 15:
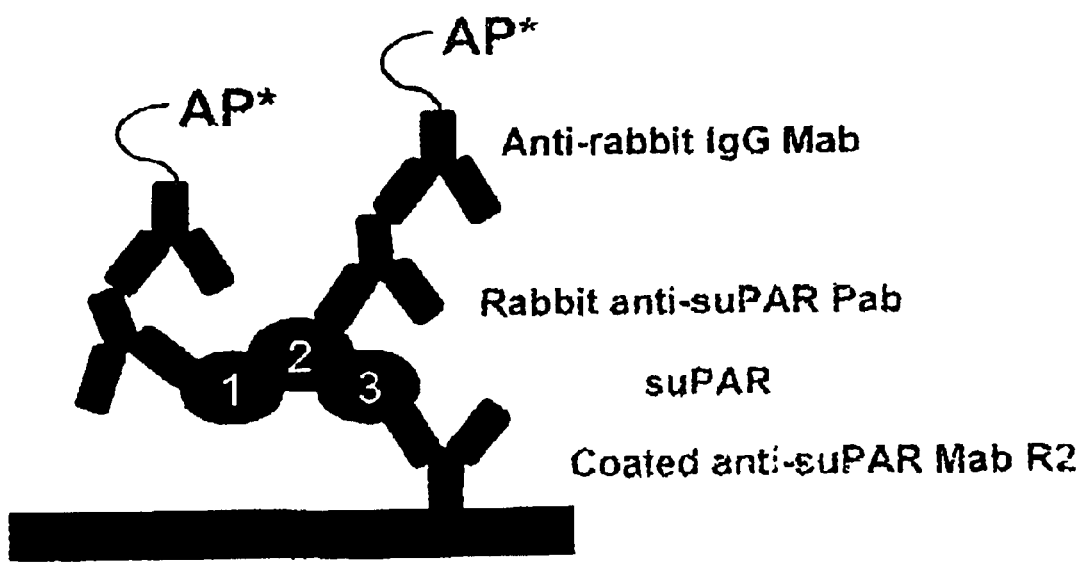
FIG. 15 shows in principle a preferred embodiment of an ELISA suitable for use in the method of the invention.

The principle of the assay is shown in FIG. 15, wherein 1, 2 and 3 designate the three fragments D1, D2 and D3 of suPAR.

Abbreviations
AP: alkaline phosphatase
Mab: monoclonal antibody

Pab: polyclonal antibody
Assay Protocol
1. Coating.
Nunc Maxisorp wells are coated with 100 μL/well of capture antibody (R2: 3.0 μg/mL).
Incubation over night at 4° C. (no shaking).
Blocking with 50% of Superblock (Pierce Chemicals) (250 μL/well).
Wash 3×.
2. Capture.
Add 100 μL/well of standards and samples diluted in Heparin Buffer.
Standards: 1, 0.5, 0.25, 0.125, 0.0625, 0.0313, 0.0156 ng/mL+blank.
Samples: diluted 1/10.
Incubation with shaking for 2 h at 30° C.
Wash 6×.
3. Detection.
Add 100 μL/well of rabbit anti-suPAR Pab diluted in Heparin buffer (1 μg/mL).
Incubation over night at +4° C. (no shaking)
Wash 6×.
4. Secondary antibody.
Add 100 μL/well of anti-rabbit IgG AP-conjugated Mab (Sigma Cat# N2556) (1/2000 dilution).
Incubation with shaking for 1 h at 30° C.
Wash 6×+3× with MilliQ-H$_2$O.
5. Substrate.
Add 100 μL/well of the freshly prepared substrate solution (p-nitrophenyl phosphate; Sigma Cat# N2765).
6. Measurement.
Continuous monitoring (kinetic measurement) at 405 nm with readings every 10 minutes until 60 minutes.

A modified assay of the above assay has the following modifications:
1. Lower coating concentration of antibody R2: 3 μg/mL→1 μL/mL.
2. Capture (sample/standard) incubation time 2 h→1 h.
3. Detection (anti-suPAR Pab) incubation time: 4° C. over night→1 h at 30° C.

Example 11 suPAR ELISA (TR-FIA)

In the following, an example of a specific ELISA suitable for use in the method of the invention is given.

Figure 16:
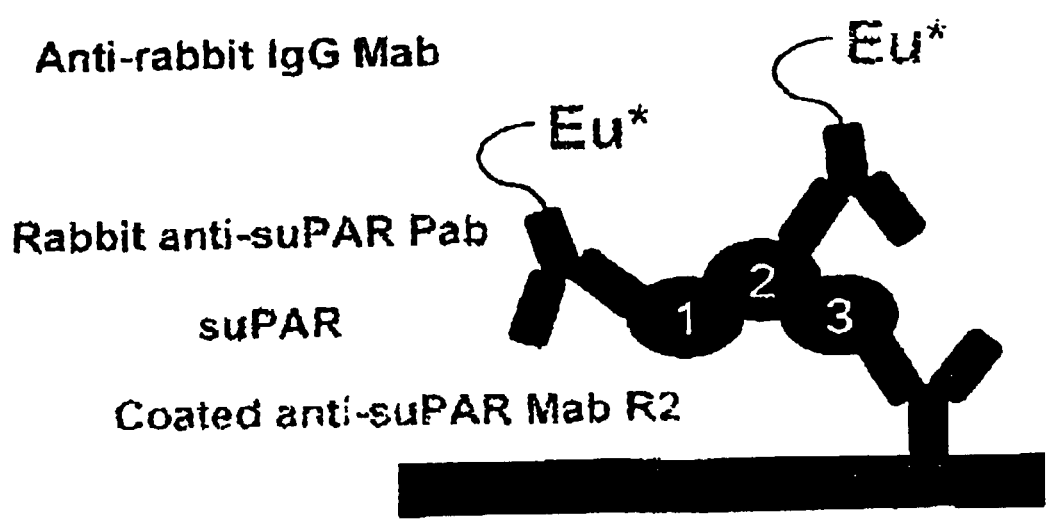
FIG. 16 shows in principle a preferred embodiment of another ELISA suitable for use in the method of the invention.

The principle of the assay is shown in FIG. 16, wherein 1, 2 and 3 designates the three fragments D1, D2 and D3 of suPAR.
Abbreviations
TR: time-resolved
FIA: fluorescence immunoassay
Eu: europium.
Mab: monoclonal antibody
Pab: polyclonal antibody
Assay Protocol
1. Coating.
Nunc Maxisorp Fluoroplate wells are coated with 100 μL/well of capture antibody (R2: 3.0 μg/mL).
Incubation over night at 4° C. (no shaking).
Blocking with 50% of Superblock (Pierce Chemicals) (250 μL/well).
Wash 3×
2. Capture.
Add 100 μL/well of standards and samples diluted in Heparin Buffer.
Standards: 1, 0.5, 0.25, 0.125, 0.0625, 0.0313, 0.0156 ng/mL+blank.
Samples: diluted 1/10.
Incubation with shaking for 2 h at 30° C.
Wash 6×.
3. Detection.
Add 100 μL/well of Eu-labelled anti-suPAR Pab diluted in Assay buffer (1 μg/mL).
Incubation over night at +4° C. (no shaking)
Wash 6×+3× with MilliQ water.
4. Enhancement.
Add 100 μL/well of the Enhancement Solution.
Incubation with shaking for 5 minutes at room temperature.
5. Measurement.
Measure time-resolved fluorescence for Eu.

Example 12

Inverted suPAR ELISA

In the following, an example of a specific ELISA suitable for use in the method of the invention is given.
Abbreviations
Mab: monoclonal antibody
Pab: polyclonal antibody
Assay Protocol
1. Coat MaxiSorp Immunoplates (Nunc 4-39454) with catching antibodies.
100 μL polyclonal anti-uPAR (2 μg/ml) diluted in coating buffer.
Incubation over night 4° C.
Monoclonal: 1 mg/ml.
2. Washing buffer 200 μL (3×).
3. Blocking buffer 200 μL. Incubation 30 minutes, 37° C., shaking.
4. Washing buffer 200 μL (3×).
5. Standard suPAR: 100 μL of 1, 0.5, 0.25, 0.12, 0.06, 0.03, 0.015 ng/ml in dilution buffer.
6. Sample dilution: sera 1:10 with dilution buffer and tissue extracts 1:20 depending on tissue.
Incubation 1 h, 37° C., shaking.
7. Washing buffer 200 μL (5×).
8. Detecting polyclonal antibody: rabbit anti-human suPAR polyclonal (1 μL/ml).
100 μL per well, incubate 1 h, 37° C., shaking.
9. Washing buffer 200 μL (5×).
10. Mouse anti-rabbit antibody/alkaline phosphatase conjugate (Sigma) (1:2000 dilution).
100 μL per well, incubate 1 h, 37° C., shaking.
11. Washing buffer 200 μL (5×).
12. MilliQ water 200 μL (3×).
13. Substrate (p-nitrophenyl phosphate; Sigma # N2765).
100 μL per well, incubate 30 minutes, RT.
Stop with 2 M NaOH.
14. Read absorbance at 405–412 nm.

Example 13

Measurement of the suPAR D1 Fragment

Urine samples from 20 HIV positive patients undergoing HAART treatment and from 10 control persons were collected. The samples were analysed for the level of suPAR/creatinine, suPAR fragment D1, CD4 T cell count and HIV mRNA using ELISA and Western blotting.

The ELISA was carried out as in Example 1.

The Western bloting was carried out using the following procedure: 100 μl of serum samples and culture medium were diluted to one ml using RIPA buffer (0.1% sodium dodecyl sulfate (SDS), 1% Triton X-100, 1% deoxycholate, 0.15 M NaCl and 0.05 M Tris-HCl pH 7.6) containing a cocktail of protease inhibitors (Complete, Boehringer, Mannheim). The samples were immunoprecipitated for 16 hours at 4° C. using biotinylated monoclonal antibodies R2, R3 or both and immobilized on streptavidin coated beads (Boehringer, Mannheim). After washing with RIPA buffer the absorbed material was eluted by boiling in non-reducing sample buffer and the proteins were separated by 12% SDS-PAGE. Proteins were transferred to PVDF membranes (Immobilon-P, Millipore) and probed with a rabbit polyclonal anti-uPAR antibody. The immune-complexes were visualized by incubation with a peroxidase conjugated donkey anti-rabbit antibody (Amersham) and chemoluminescent detection (SuperSignal Ultra, Pierce Chemicals).

The results are shown in FIGS. 17–20.

From FIG. 17 it may be concluded that the level of suPAR is significantly higher for the HIV positive group than for the control group (p=0.003).

FIGS. 18 and 19 show that the presence of D1 is independent from the CD4 T cell count and the suPAR level, respectively.

FIG. 20 shows that the presence of D1 significantly correlates to the level of HIV mRNA. Also, the presence of D1 is significantly more often found in patients who have detectable HIV RNA.

Only one person from the control group had a detectable level of D1.

Example 14

The Expression of uPAR on PBMC Correlates with Serum Level of suPAR

Background. The aim of this example is to determine whether there is a significant relationship between surface expression of uPAR and serum level of suPAR.

Methods: Blood was collected from 10 healthy blood donors attending the donor clinic at Hvidovre Hospital. The serum was collected and suPAR concentration measured using ELISA. Peripheral blood mononuclear cells (PBMC) was collected using Histopaq gradient centrifugation, and the expression of CD87 was measured using R2 antibody and a secondary FITC conjugated antibody against mouse antibody. An idiotypic negative control antibody was included as a control of specificity.

Results: The results are shown in FIG. 21. The Y-axis on the left show the serum level of suPAR (ng/ml). The Y-axis on the right shows the percentage of cells expressing the uPAR receptor (CD87 positive cells). All blood donors had measurable uPAR receptor on the PBMC and measurable suPAR in serum. In eight of ten patients (p<0.05), the suPAR level significantly correlated with the uPAR surface expression.

Discussion. The results show a significant relationship between PBMC surface expression of uPAR (CD87) and the serum level of suPAR. Thus, it is therefore reasonable to assume that the surface expression of uPAR is a strong prognostic factor in HIV infection. The use of uPAR as a marker involves the advantage that uPAR can be measured along with the CD4 T cell count, e.g. by FACS, in routine measurements of HIV infected individuals and thereby add valuable information regarding the patients progression status.

LIST OF REFERENCES

1. Blasi F. uPA, uPAR, PAI-1: key intersection of proteolytic, adhesive and chemotactic highways? Immunol Today 1997 September; 18(9):415–7
2. Min H Y, Semnani R, Mizukami I F, Watt K, Todd R F 3d, Liu D Y. cDNA for Mo3, a monocyte activation antigen, encodes the human receptor for urokinase plasminogen activator. J Immunol 1992 Jun. 1; 148(11):3636–42
3. Nykjaer A, Moller B, Todd R F 3rd, Christensen T, Andreasen P A, Gliemann J, Petersen C M. Urokinase receptor. An activation antigen in human T lymphocytes. J Immunol 1994 Jan. 15; 152(2):505–16
4. Frank I, Stoiber H, Godar S, Stockinger H, Steindl F, Katinger H W, Dierich M P. Acquisition of host cell-surface-derived molecules by HIV-1. AIDS 1996 December; 10(14):1611–20
5. Speth C, Pichler I, Stockl G, Mair M, Dierich M P. Urokinase plasminogen activator receptor (uPAR; CD87) expression on monocytic cells and T cells is modulated by HIV-1 infection. Immunobiology 1998 July; 199(1): 152–62
6. Wilhelm O G, Wilhelm S, Escott G M, Lutz V, Magdolen V, Schmitt M, Rifkin D B, Wilson E L, Graeff H, Brunner G. Cellular glycosylphosphatidylinositol-specific phospholipase D regulates urokinase receptor shedding and cell surface expression. J Cell Physiol 1999 August; 180(2):225–35
7. Pedersen N, Schmitt M, Ronne E, Nicoletti M I, Hoyer-Hansen G, Conese M, Giavazzi R, Dano K, Kuhn W, Janicke F, et al. A ligand-free, soluble urokinase receptor is present in the ascitic fluid from patients with ovarian cancer. J Clin Invest 1993 November; 92(5):2160–7
8. Ronne E, Hoyer-Hansen G, Brunner N, Pedersen H, Rank F, Osborne C K, Clark G M, Dano K, Grondahl-Hansen J. Urokinase receptor in breast cancer tissue extracts. Enzyme-linked immunosorbent assay with a combination of mono- and polyclonal antibodies. Breast Cancer Res Treat 1995 March; 33(3):199–207
9. Stephens R W, Pedersen A N, Nielsen H J, Hamers M J, Hoyer-Hansen G, Ronne E, Dybkjaer E, Dano K, Brunner N. ELISA determination of soluble urokinase receptor in blood from healthy donors and cancer patients. Clin Chem 1997 October; 43(10):1868–76
10. Sier C F, Stephens R, Bizik J. Mariani A, Bassan M, Pedersen N, Frigerio L, Ferrari A, Dano K, Brunner N, Blasi F. The level of urokinase-type plasminogen activator receptor is increased in serum of ovarian cancer patients. Cancer Res 1998 May 1; 58(9):1843–9
11. Chavakis T, Kanse S M, Yutzy B, Lijnen H R, Preissner K T. Vitronectin concentrates proteolytic activity on the cell surface and extracellular matrix by trapping soluble urokinase receptor-urokinase complexes. Blood 1998 Apr. 1; 91(7):2305–12
12. Stephens R W, Nielsen H J, Christensen I J, Thorlacius-Ussing O, Sorensen S, Dano K, Brunner N. Plasma urokinase receptor levels in patients with colorectal cancer: relationship to prognosis. J Natl Cancer Inst 1999 May 19; 91 (10):869–74
13. Wahlberg K, Hoyer-Hansen G, Casslen B. Soluble receptor for urokinase plasminogen activator in both full-length and a cleaved form is present in high concentration in cystic fluid from ovarian cancer. Cancer Res 1998 Aug. 1; 58(15):3294–8
14. Sier C F, Sidenius N, Mariani A, Aletti G, Agape V, Ferrari A, Casetta G, Stephens R W, Brunner N, Blasi F. Presence of urokinase-type plasminogen activator receptor in urine of cancer patients and its possible clinical relevance. Lab Invest 1999 June; 79(6):717–22
15. Ninomiya H, Hasegawa Y, Nagasawa T, Abe T. Excess soluble urokinase-type plasminogen activator receptor in the plasma of patients with paroxysmal nocturnal hemoglobinuria inhibits cell-associated fibrinolytic activity. Int J Hematol 1997 April; 65(3):285–91
16. Mustjoki S, Alitalo R, Stephens R W, Vaheri A. Blast cell-surface and plasma soluble urokinase receptor in acute leukemia patients: relationship to classification and response to therapy. Thromb Haemost 1999 May; 81(5): 705–10
17. Holst-Hansen C, Hamers M J, Johannessen B E, Brunner N, Stephens R W. Soluble urokinase receptor released from human carcinoma cells: a plasma parameter for xenograft tumour studies. Br J Cancer 1999 September; 81(2):203–11
18. Ullum H, Lepri A C, Katzenstein T L, Phillips A N, Skinhoj P, Gerstoft J, Pedersen B K. Prognostic value of single measurements of beta-2-microglobulin, immunoglobulin A in HIV disease after controlling for CD4 lymphocyte counts and plasma HIV RNA levels. Scand J Infect Dis 2000; 32(4):371–6
19. Christensen J K, Eugen-Olsen J, Sorensen M, Ullum H, Gjedde S B, Pedersen B K, Nielsen J O, Krogsgaard K. Prevalence and prognostic significance of infection with TT virus in patients infected with human immunodeficiency virus. J Infect Dis 2000 May; 181(5):1796–9
20. Cozzi Lepri A, Katzenstein T L, Ullum H, Phillips A N, Skinhoj P, Gerstoft J, Pedersen B K. The relative prognostic value of plasma HIV RNA levels and CD4 lymphocyte counts in advanced HIV infection. AIDS 1998 Sep. 10; 12(13): 1639–43
21. Ullum H, Cozzi Lepri A, Victor J, Aladdin H, Phillips A N, Gerstoft J, Skinhoj P, Pedersen B K. Production of beta-chemokines in human immunodeficiency virus (HIV) infection: evidence that high levels of macrophage inflammatory protein-1beta are associated with a decreased risk of HIV disease progression. J Infect Dis 1998 February; 177(2): 331–6.
22. Ullum H, Lepri A C, Victor J, Skinhoj P, Phillips A N, Pedersen B K. Increased losses of CD4+ CD45RA+cells in late stages of HIV infection is related to increased risk of death: evidence from a cohort of 347 HIV-infected individuals. AIDS 1997 October; 11(12):1479–85
23. Ullum H, Cozzi Lepri A, Bendtzen K, Victor J, Gotzsche P C, Phillips A N, Skinhoj P, Klarlund Pedersen B. Low production of interferon gamma is related to disease progression in HIV infection: evidence from a cohort of 347 HIV-infected individuals. AIDS Res Hum Retroviruses 1997 Aug. 10; 13(12):1039–46
24. Ullum H, Victor J, Katzenstein T L, Gerstoft J, Gotzsche P C, Bendtzen K, Skinhoj P, Pedersen B K. Decreased short-term production of tumor necrosis factor-alpha and interleukin-1beta in human immunodeficiency virus-seropositive subjects. J Infect Dis 1997 June; 175(6): 1507–10
25. Ullum H, Gotzsche P C, Victor J, Dickmeiss E, Skinhoj P, Pedersen B K. Defective natural immunity: an early manifestation of human immunodeficiency virus infection. J Exp Med 1995 Sep. 1; 182(3):789–99
26. N. Sidenius, C. F. M. Sier, H. Ullum, B. K. Pedersen, A. C. Lepri, F. Blasi, and J. Eugen-Olsen. Serum level of soluble urokinase-type plasminogen activator receptor is a strong and independent predictor of survival in human immunodeficiency virus infection. Blood 2000, 96 (13).
27. Handley M A, Steigbigel R T, Morrison S A. A role for urokinase-type plasminogen activator in human immunodeficiency virus type 1 infection of macrophages. J Virol 1996; 70(7):4451–4456.
28. Nykjaer A, Conese M, Christensen E I, Olson D, Cremona O, Gliemann J et al. Recycling of the urokinase receptor upon internalization of the uPA:serpin complexes. EMBO J. 1997; 16(10):2610–2620.
29. Ye S, Green F R, Scarabin P Y, Nicaud V, Bara L, Dawson S J et al. The 4G/5G genetic polymorphism in the promoter of the plasminogen activator inhibitor-1 (PAI-1) gene is associated with differences in plasma PAI-1 activity but not with risk of myocardial infarction in the ECTIM study. Etude CasTemoins de I'nfarctus du Mycocarde. Thromb Haemost 1995; 74(3):837–841.
30. Eugen-Olsen J, Iversen A K, Garred P, Koppelhus U, Pedersen C, Benfield T L et al. Heterozygosity for a deletion in the CKR-5 gene leads to prolonged AIDS-free survival and slower CD4 T-cell decline in a cohort of HIV-seropositive individuals. AIDS 1997; 11(3): 305–310.
31. Sidenius N, Sier C F, Blasi F. Shedding and cleavage of the urokinase receptor (uPAR): identification and characterisation of uPAR fragments in vitro and in vivo. FEBS Lett 2000; 475(1): 52–56.
32. Lisse I M, Whittle H, Aaby P, Normark M, Gyhrs A, Ryder L P. Labelling of T cell subsets under field conditions in tropical countries. Adaptation of the immunoalkaline phosphatase staining method for blood smears. J Immunol Methods 1990; 129(1):49–53.
33. Lisse I M, Bottiger B, Christensen L B, Knudsen K, Aaby P, Gottschau A et al. Evaluation of T cell subsets by an immunocytochemical method compared to flow cytometry in four countries. Scand J Immunol 1997; 45(6):637–644.
34. Chapman H A. Plasminogen activators, integrins, and the coordinated regulation of cell adhesion and migration. Curr Opin Cell Biol. 1997;9:714–724.
35. Plesner T, Behrendt N, Ploug M. Structure, function and expression on blood and bone marrow cells of the urokinase-type plasminogen activator receptor, uPAR. Stem Cells. 1997;15:398–408.
36. Gyetko M R, Chen G H, McDonald R A, et al. Urokinase is required for the pulmonary inflammatory response to *Cryptococcus neoformans*. A murine transgenic model. J Clin Invest. 1996;97:1818–1826.
37. May A E, Kanse S M, Lund L R, Gisler R H, Imhof B A, Preissner K T. Urokinase receptor (CD87) regulates leukocyte recruitment via beta 2 integrins in vivo. J Exp Med. 1998;188:1029–1037.
38. Gyetko M R, Libre E A, Fuller J A, Chen G-H, Toews G B. Urokinase is required for T lymphocyte proliferation and activation in vitro. J Lab Clin Med. 1999; 133:274–288.
39. Dane K, Andreasen P A, Grøndahl Hansen J, Kristensen P, Nielsen L S, Skriver L. Plasminogen activators, tissue degradation, and cancer. Adv Cancer Res. 1985; 44:139–266.

What is claimed is:

1. A method of prognosticating HIV infection in a subject comprising the steps of
   (a) taking a serum, blood, or urine sample from an HIV infected subject,
   (b) performing in vitro a measurement of the level in the serum, blood, or urine sample of soluble urokinase plasminogen activator receptor (suPAR), and
   (c) using the measurement value obtained to evaluate and provide prognosis for the subject.

2. A method according to claim 1, wherein step (b) is effected by means of a stick.

3. A method according to claim 1, wherein step (b) is effected using ELISA.

4. A method according to claim 1, wherein the subject evaluated is in treatment.

5. A method according to claim 1, wherein the subject is in highly active anti-retroviral therapy (HAART).

6. A method of prognosticating HIV infection in a subject comprising the steps of
   (a) taking a blood sample from an HIV infected subject,
   (b) performing in vitro a measurement of the level in the blood sample of peripheral blood mononuclear cell (PBMC)-bound urokinase plasminogen activator receptor (uPAR), and
   (c) using the measurement value obtained to evaluate and provide prognosis for the subject.

7. A method according to claim 6, wherein the subject evaluated is in treatment.

8. A method according to claim 6, wherein the subject is in highly active anti-retroviral therapy (HAART).

9. A method of prognosticating HIV infection in a subject comprising the steps of
   (a) taking a serum or blood sample from an HIV infected subject,
   (b) performing in vitro a measurement of the level in the serum or blood sample of the soluble urokinase plasminogen activator receptor (suPAR) fragment D1, and
   (c) using the measurement value obtained to evaluate and provide prognosis for the subject.

10. A method according to claim 9, wherein step (b) is effected by means of a stick.

11. A method according to claim 9, wherein step (b) is effected using ELISA.

12. A method according to claim 9, wherein the subject evaluated is in treatment.

13. A method according to claim 9, wherein the subject is in highly active anti-retroviral therapy (HAART).

* * * * *